(12) United States Patent
Nguyen et al.

(10) Patent No.: US 7,630,791 B2
(45) Date of Patent: Dec. 8, 2009

(54) SYSTEM AND METHOD FOR STORING ITEMS AND TRACKING ITEM USAGE

(75) Inventors: Thuy T. Nguyen, Carlsbad, CA (US); Richard W. Massey, Encinitas, CA (US)

(73) Assignee: CareFusion 303 Inc., San Diego, CA (US)

( * ) Notice: Subject to any disclaimer, the term of this patent is extended or adjusted under 35 U.S.C. 154(b) by 388 days.

(21) Appl. No.: 11/298,813

(22) Filed: Dec. 9, 2005

(65) Prior Publication Data

US 2007/0135965 A1 Jun. 14, 2007

(51) Int. Cl.
*G06F 17/00* (2006.01)

(52) U.S. Cl. .................. 700/242; 700/236; 700/243; 700/244

(58) Field of Classification Search ................. 700/242
See application file for complete search history.

(56) References Cited

U.S. PATENT DOCUMENTS

| | | | |
|---|---|---|---|
| 4,847,764 | A | 7/1989 | Halvorson |
| 5,805,455 | A | 9/1998 | Lipps |
| 5,905,653 | A * | 5/1999 | Higham et al. ............... 700/242 |
| 6,151,536 | A | 11/2000 | Arnold et al. |
| 6,338,007 | B1 | 1/2002 | Broadfield et al. |
| 6,636,780 | B1 | 10/2003 | Haitin et al. |
| 6,640,159 | B2 * | 10/2003 | Holmes et al. ............... 700/242 |
| 6,658,322 | B1 | 12/2003 | Frederick et al. |
| 6,847,861 | B2 | 1/2005 | Lunak et al. |
| 6,850,337 | B1 | 2/2005 | Anderson et al. |
| 7,146,247 | B2 * | 12/2006 | Kirsch et al. ................. 700/242 |
| 7,251,546 | B2 * | 7/2007 | Chirnomas ................... 700/242 |
| 2001/0032035 | A1 | 10/2001 | Holmes et al. |
| 2003/0120384 | A1 * | 6/2003 | Haitin et al. ................. 700/242 |
| 2003/0164401 | A1 | 9/2003 | Andreasson et al. |
| 2005/0062238 | A1 | 3/2005 | Broadfield et al. |
| 2005/0067420 | A1 | 3/2005 | Diaz et al. |
| 2005/0125097 | A1 | 6/2005 | Chudy et al. |
| 2005/0131579 | A1 | 6/2005 | Andreasson et al. |

FOREIGN PATENT DOCUMENTS

| | | |
|---|---|---|
| WO | 0023908 A1 | 4/2000 |
| WO | 2004014189 A1 | 2/2004 |

* cited by examiner

*Primary Examiner*—Gene Crawford
*Assistant Examiner*—Timothy R Waggoner
(74) *Attorney, Agent, or Firm*—McDermott Will & Emery LLP

(57) ABSTRACT

A system and method for storing items and tracking usage of items in a user configurable medication dispensing cabinet is disclosed. Items are stored in a tray or drawer having user-adjustable storage spaces. A graphical user interface comprising a touch screen enables users to rapidly customize the layout of storage spaces, which allows a wide variety of shapes and sizes of items to be stored in the tray. A kit of items that are identified in advance may be removed more efficiently by ordering removal based on the location of the storage spaces in which the items are stored. Items not identified in advance may be removed and tracked more efficiently through the use of the graphical user interface or a scanner for reading machine-readable identification tags on the items or the storage spaces. Bar codes and RFID devices are contemplated for use as identification tags.

29 Claims, 18 Drawing Sheets

FIG. 28

Patient Case-Remove Med for "BRONZE, MICHAEL" (DOB: 06/08/1961)
ALLERGY: UNKNOWN SEE PATIENT'S CHART

A B C D E F G H I JK L M N O P QR S T UV WX YZ

Select Med by System Category    Select Med from ANALGESIA:    Selected Summary:

[System Category]  [My Kits]  [System Kits]

FENTANYL 0.1 MG/2 ML VIAL
  SUBLIMAZE
  QTY: 1 VIAL

AMNESIA SEDATION

ANALGESIA

ANTI-HYPERTENSIONS    KETAMINE 200 MG/20 ML INJECTION
                       KETAMAR
                       QTY: 1 INJECTION

EMERGENCY             KETAMINE 500 MG/10 ML INJECTION
                       KETAMAR
                       QTY: 1 INJECTION

LOCAL                 KETAMINE 500 MG/5 ML INJECTION
                       KETAMAR
                       QTY: 1 INJECTION

MISCELLANEOUS         MORPHINE SULFATE 10 MG/2 ML INJECTION
                       MORPHINE SULFATE
                       QTY: 1 INJECTION

OB DRUGS              MORPHINE PF1 MG/2 ML INJECTION
                       ASTRMORPH/PF
                       QTY: 1 INJECTION

REVERSAL              REMIFENTANIL 1 MG
                       REMIFENTANIL
                       QTY: 1

Item    Qty

1106

1102

[Dispense]  [Patient Case]    [Select Patient]  [Main Menu]

1100
1116

SYSTEM AND METHOD FOR STORING ITEMS AND TRACKING ITEM USAGE

FIELD OF THE INVENTION

The present invention relates generally to medication dispensing machines or stations. More particularly, the present invention relates to a system and method for storing and tracking usage of drugs and other items such as may be used in a hospital or other healthcare institution.

BACKGROUND OF THE INVENTION

Medication management systems comprising dispensing stations have been known for a number of years, and by way of example, a form of a such system is described in U.S. Pat. No. 6,021,392, the entire contents of which are incorporated by reference herein. Dispensing stations or stations are typically used by healthcare institutions to efficiently store, track, and document the usage of drugs and related items. In addition to tracking drug and device quantities, dispensing stations track patient information as well as expiration dates and lot numbers of items stored within them. Functioning as mobile satellites of a pharmacy, the dispensing stations are often located at numerous points throughout a facility in order to provide authorized users, such as nurses, doctors, and other caregivers controlled and convenient access to drugs and supplies.

Items are typically stored in dispensing station drawers which may be locked depending on the nature of the items inside. Dispensing drawers may be further partitioned into a number of sections or containers within each drawer. For example, such partitions may result in drawer containers that are consecutive with one another along the sliding direction of the drawer. Graduated access to containers toward the rear of such drawers has been controlled by limiting the extent to which an unlocked drawer may slide out of its cabinet.

Alternatively, drawers have comprised a number of modular, individually removable containers of varying size that can be locked down onto the floor of drawer. The modules can have separate lockable lids, allowing the modules to be filled with items at a location remote from the dispensing station, such as in a pharmacy, and later installed in the dispensing station drawer. Unlocking of drawers and individual container lids at the dispensing station is typically handled by a control unit having a user interface, such as a keyboard and/or touch sensitive display screen mounted on the dispensing station. A user interacts with the interface to select the item he or she wishes to access. The interface also cooperates with a processor to provide electrical signals to open or unlock the selected drawer or lid so that the user may take the selected medication or item for administration to a patient.

Prior dispensing stations have allowed the user to search for and obtain a particular item by entering a personal identifier and password (i.e., logging on), and then scrolling through a pick list of available items shown on a display screen or by inputting the name of the item using a keyboard. Where the item is available and the user is recognized as having the proper authority, a drawer number and container number are indicated on the display screen and, if necessary, the control unit unlocks the corresponding drawer. Alternatively, illuminated lights on the drawer have been used to indicate the location of the appropriate container. When the drawer is closed, the control unit records the time of the transaction, item description, quantity taken, name of the user, etc. In prior art systems, the transaction record relies upon the user removing the correct item from the correct container. Although the user may later recognize that the wrong item was removed, the user must perform an additional transaction to return the item to the drawer.

Management of medication during anesthesia presents unique challenges. Because anesthesia involves the use of controlled, narcotic medications, healthcare institutions must implement strict documentation and record keeping of usage to avoid substantial monetary fines and the possible loss of accreditation. Automated management processes and systems in anesthesia are well known, an example of which is found in U.S. Pat. No. 6,339,732, which is incorporated in its entirety by reference herein.

In general, most items and medications to used during surgery are taken from anesthesia dispensing stations in advance of the surgical procedure. The anesthesiologist administers medication based on the present condition of the patient and must be able to readily obtain and administer additional quantities or current medications as well as additional medications as needed to respond to unforeseen or changing circumstances during surgery while adhering to the institution's strict record keeping and control procedures. Accordingly, the drawers of the dispensing station in a surgical suite are typically kept open or unlocked during a surgical procedure to provide ready access to the stored medications by the anesthesiologist. Since the items stored in the dispensing station drawers are often in plain view, the location of many of the items is known in advance by the anesthesiologist. As such, it is inefficient to require the anesthesiologist to pre-select or identify an item through the use of a keyboard or pick list as is done in prior art systems because such a process requires time that may not be available when the anesthesiologist needs a particular medication to respond to a rapidly developing or changing situation. Furthermore, when several items are dispensed in response to an unexpected situation, identification of the items through a keyboard or pick list is prone to human error and is likely to be deferred until a later, more convenient time. At such a later time, it is not unusual for some details of the transaction to have been forgotten.

Many items stored in dispensing stations, such as general supplies, are of a type that requires little or no control, are varied in size, and are often packaged together in packs customized for a type of situation or surgical procedure, such as, for example, pediatric, cardiac and neurological procedures. In addition, some items are used more frequently than others and thus may require greater quantities to be stocked within the dispensing station. To address this need, attempts have been made to make drawers in dispensing stations configurable by the user. For instance, drawers have been divided into zones with partitions between each zone being removable to create containers of variable size comprising one or more zones. A limiting factor with configurable drawers is that the means for informing the user of the location of a container holding a desired item must adapt to changing drawer configurations. One prior solution to this problem involved mounting a light adjacent each zone and then illuminating certain of the lights to inform the user of the container from which an item was removed. When that container encompasses five zones, for example, the five lights adjacent the five zones may be illuminated to indicate the location of the appropriate container.

Another disadvantage of configurable drawers is that the means of controlling and tracking access to an item must adapt to changing container configurations. One prior solution to this problem mounted a "take" switch adjacent each zone in the drawer. When removing an item from the drawer, the user is required to actuate the take switch a multiple of times corresponding to the quantity removed from the corresponding container. A "cancel" switch is employed to cancel or indicate a quantity returned to the drawer. For example, when a container encompasses ten zones, the user removing medication may be required to actuate one of the ten take switches adjacent the ten zones.

The cost of a dispensing station typically increases with the number of lights and switches on any given drawer. The amount of electrical wiring and components subject to wear or malfunction also increases with the number of lights and switches. Moreover, without a quick and convenient means of verification, tracking errors are more likely to occur when a user, distracted by the pressure of a sudden and unforeseen event, takes an item from the wrong container, presses the wrong switch on the drawer, or presses the switch an incorrect number of times.

As mentioned above, some prior art dispensing stations control the extent to which its drawer slides open in order to prevent access to containers in the rear of the drawer. A configurable drawer may have multiple longitudinal columns of containers with each column having independently movable transverse partitions, which can result in an irregular pattern of partitions. For example, a drawer may have to slide out eight inches in order to allow access to the second container in one column, but the drawer may have to slide out eleven inches in order to allow access to the second container in another column. Thus, having configurable drawers may be disadvantageous in that the control unit on the dispensing station must adapt to irregular drawer configurations. Moreover, a user may be unlikely to reconfigure a drawer if it requires complicated or time consuming reprogramming of the control unit.

Accordingly, those skilled in the art have recognized a need for a system and method for storing items and tracking item usage that provide greater flexibility and ease in reconfiguring the number, size, and location of containers in storage drawers of a medication dispensing cabinet while reducing the potential for tracking errors to occur. The present invention satisfies these and other needs.

SUMMARY OF THE INVENTION

The present invention provides for a system and method for storing items and tracking item usage. Briefly and in general terms, the system comprises a drawer having a plurality of storage spaces adjustable to accommodate various sized items, an input means for inputting drawer configuration information and storage space location information, a control unit in operable communication with the drawer and programmed to receive inputs from a user to adjust the configuration of the drawers, including locations of the storage spaces, a memory in operable communication with a processor to store storage space-specific information and item-specific information, the storage space-specific information including storage space location information and drawer configuration information, a display screen in communication with the control unit, the display screen configured to display an image representative of the storage space-specific information stored by the control unit.

In detailed aspects, the image representative of the storage space-specific information includes a graphical representation of the drawer and locations of the storage spaces relative to one another. In other detailed aspects, the processor is further programmed to generate a transaction record when the user inputs storage space-specific information, the transaction record comprising at least a description and a numerical quantity of items placed into a selected storage space. In further aspects, the transaction record further comprises a description and a numerical quantity of items removed from the selected storage space. In yet other detailed aspects, the display screen is configured to display a preliminary image that is user-modifiable to communicate storage space-specific information to the control unit.

Turning now to other detailed aspects, the system further comprises a machine-readable identification tag affixed to an item, and a scanner in communication with the control unit, the scanner configured to read the tag. In yet other detailed aspects, the system further comprises a machine-readable identification tag affixed to one of the plurality of storage spaces, and a scanner in communication with the control unit, the scanner configured to read the tag. In further aspects, the machine-readable identification tag is configured to store and communicate item-specific information.

In another aspect of the invention, a system for storing items and tracking item usage comprises a tray having a plurality of storage spaces for storing items, one or more of the storage spaces having partitions that are user-adjustable a control unit configured to store storage space-specific information and item-specific information, and configured to generate transaction records, and a graphical user interface in communication with the control unit, the graphical user interface including a user-defined touch-sensitive image representative of the storage space-specific information stored by the control unit and for inputting and editing storage space-specific information.

In other detailed aspects, the touch-sensitive image depicts a graphical representation of the tray and positions of the partitions contained therein. In further aspects, when the user touches a portion of the touch-sensitive image corresponding to a selected storage space on the tray, the control unit creates a transaction record comprising at least a description and a numerical quantity of items placed into the selected storage space. In other aspects, when the user touches a portion of the touch-sensitive image corresponding to a selected storage space on the tray, the control unit creates a transaction record comprising at least a description and a numerical quantity of items removed from the selected storage space. In more detailed aspects, the graphical user interface is configured to display a preliminary image that is capable of being modified to communicate storage space-specific information to the control unit.

Turning now to yet other detailed aspects, the system further comprises a machine-readable identification tag affixed to an item, and a scanner in communication with the control unit, the scanner configured to read the tag. In other detailed aspects, the system further comprises a machine-readable identification tag affixed to one of the plurality of storage spaces, and a scanner in communication with the control unit, the scanner configured to read the tag. In even more detailed aspects, the machine-readable identification tag is configured to store and communicate item-specific information.

Also provided is a method for configuring a medication dispensing drawer to have various sized storage spaces, the comprising providing a graphical representation of a current drawer configuration, the graphical representation including at least one location where a storage space may be located, identifying a first corner of a desired storage space location, identifying a second corner of the desired storage space location, updating the graphical representation to show an identified storage space location, and storing the identified storage space location in a memory.

In more detailed aspects, the method further comprises receiving storage space-specific information from a graphical user interface, associating the storage space with a selected item to be stored in the storage space, storing the selected item in the storage space, dispensing the selected item from the storage space, and generating a transaction record.

Other features, aspects, and advantages of the present invention will become apparent from the following detailed description, taken in conjunction with the accompanying drawings, which illustrate, by way of example, the principles of the invention.

BRIEF DESCRIPTION OF THE DRAWINGS

FIG. 28 is a graphical representation of a Medication Selection screen showing a list of system kits and items comprising an analgesia system kit.

DETAILED DESCRIPTION OF THE PREFERRED EMBODIMENTS

Figure 1:
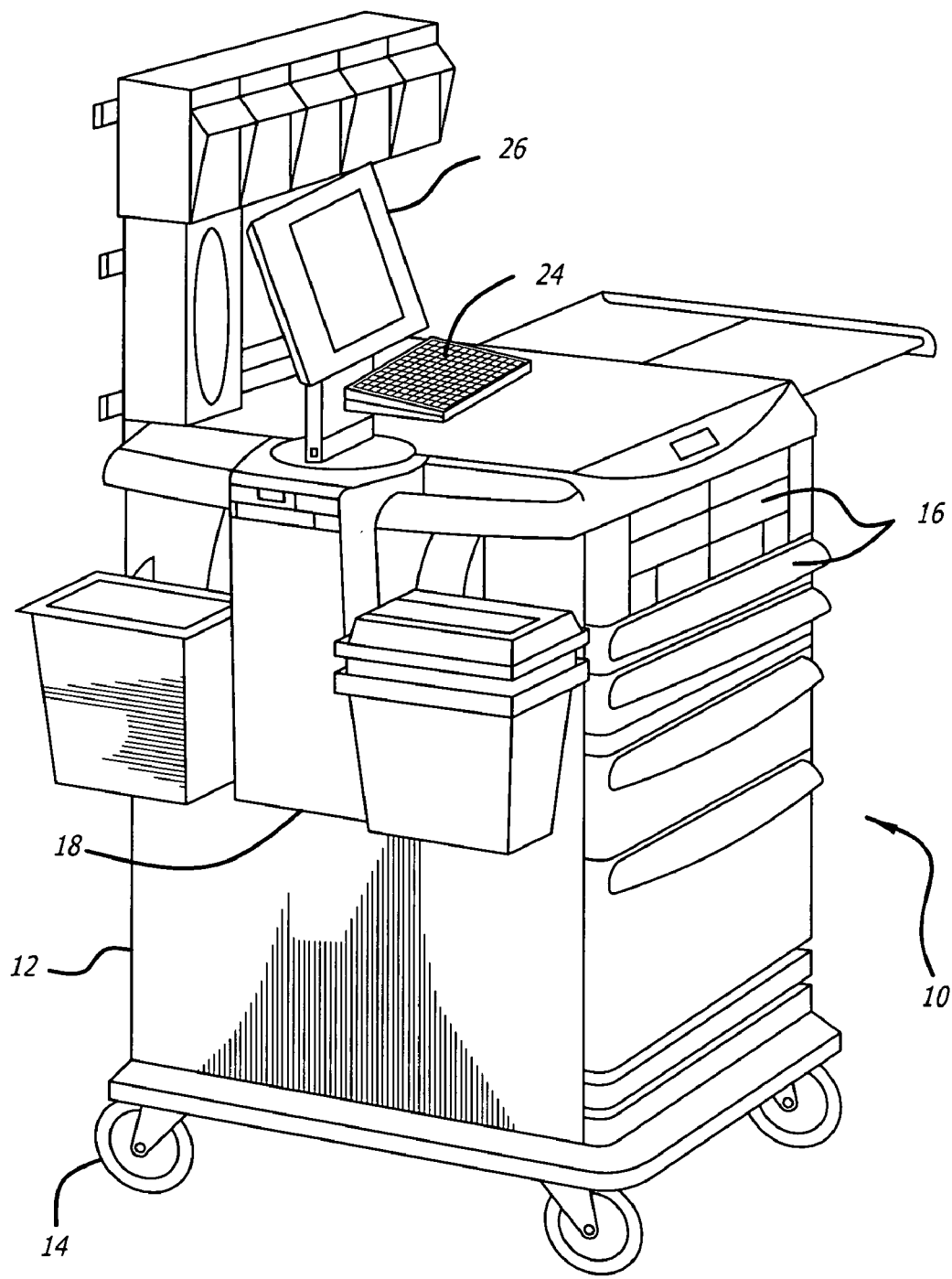
FIG. 1 is a perspective view of a dispensing station and shows a display screen, a keyboard and a plurality of drawers.

As shown in the exemplary drawings, wherein like reference numerals designate corresponding or like elements among the several views, the present invention is embodied in a mobile or stationary dispensing station 10 that is used in an institution to controllably dispense medication and other items for use in treating patients. Preferably, as shown in FIG. 1, the dispensing station is a cabinet 12 supported by wheels 14 so that it may be moved easily throughout a facility, such as an operating room. In the exemplary embodiment shown, the cabinet holds sliding trays or drawers 16 of varying shapes and sizes for storing a wide variety of items. The number and configuration of the drawers may be modified as needed to meet the needs of the institution in which the dispensing station is used.

Figure 2:
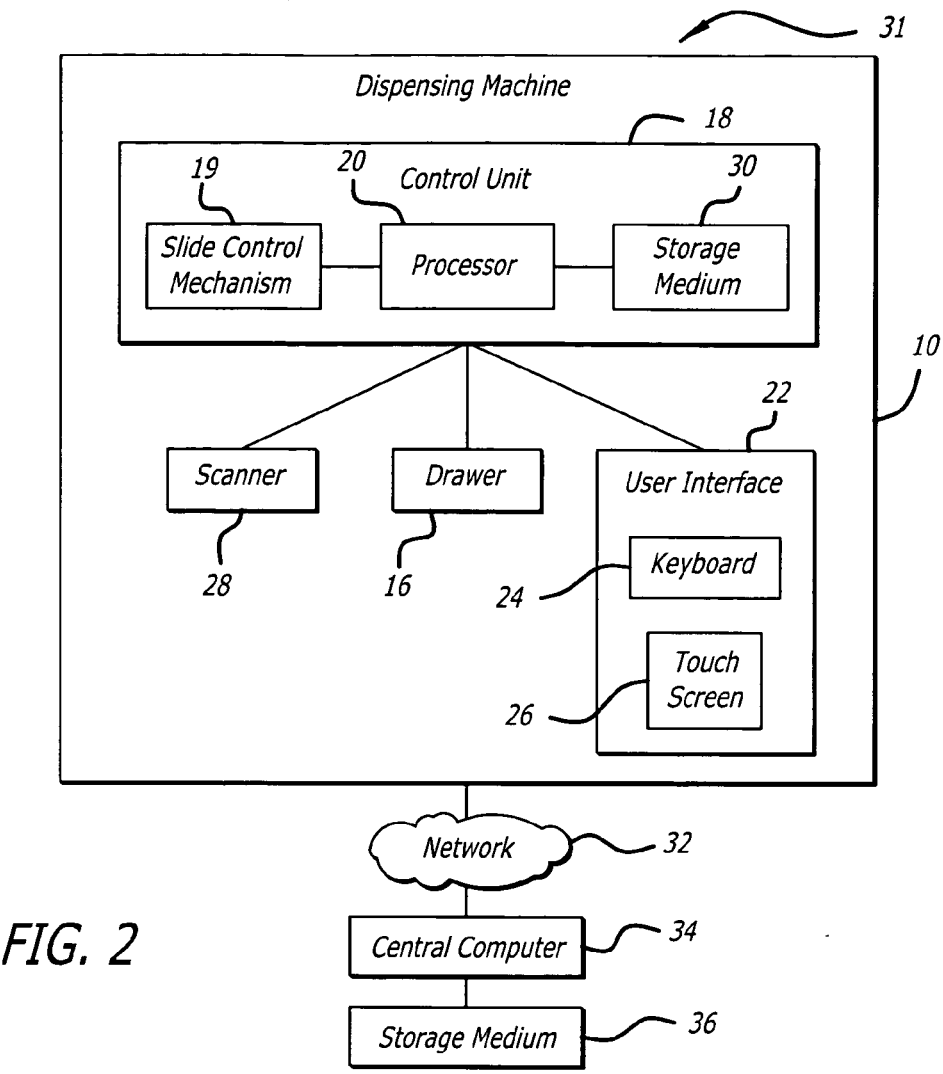
FIG. 2 is a block diagram of an operating system of the dispensing station of FIG. 1 for storing and tracking items and shows a network connection between the dispensing station of FIG. 1, a central computer, and a storage medium.

FIG. 2 is a schematic drawing of the dispensing cabinet illustration various portions and sub-systems of the cabinet. Drawers 16 are coupled to a control unit 18 for limiting and tracking user access to stored items. The control unit comprises a slide control mechanism 19 with locking hardware, such as solenoids, latches, and/or muscle wires, controlled by a processor 20 in electronic communication with a user interface 22. The user interface comprises a keyboard 24 and a display screen. Preferably, the display screen is a touch screen 26, which allows a user to interact with images displayed on the screen to input data and commands for use by the processor to control the operation of the cabinet. Persons of ordinary skill in the art will appreciate that a mouse or other pointing device (not shown) may be used in combination with the touch screen 26 to interact with images displayed on the screen. A device such as a scanner 28 for reading machine-readable identification tags on storage spaces and/or on items to be stored may be in electronic communication with the control unit so as to provide the control unit with information regarding the items to be stored in the drawers. As will be described in more detail below, machine readable labels or tags may also contain information related to the configuration of the drawers and storage spaces therein. A memory storage medium 30 associated with the processor may store information regarding the items and the configuration of the drawers. The storage medium may, for example, be a hard disc drive or non-volatile storage device.

As shown in FIG. 2, the dispensing station 10 is part of a system 31 and is linked via a network 32, such as the Internet and/or local area network, to a central computer 34 with access to a storage medium 36, such as, for example, a plurality of databases having patient-specific information and information regarding items to be stored in the dispensing station. The network provides a means for the control unit 18 to automatically obtain patient-specific information and information regarding stored items. Such network communication may be made through conventional wire connections, fiber optic connections, or through wireless methods, such as, for example, methods utilizing IEEE 802.11 (e.g., Wireless Fidelity), IEEE 802.15 (e.g., Bluetooth), and IrDA-based (Infrared Data Association) standards.

The drawers 16 of cabinet 10 (FIG. 1) may be of a secured, semi-secured, or unsecured type depending on their contents. Any combination of these drawer types may be used. Typically, secured-type drawers are for storing narcotic medications and other controlled substances, and remain locked until a user requests an item and follows a procedure for accessing the contents of a drawer, such as logging on, requesting a particular amount of a medication, and assigning use to a particular patient. When such a request is made, only the particular secured-type drawer containing the requested item is unlocked temporarily so that the drawer maybe opened. When the secured-type drawer is closed, it is locked automatically by the control unit 18 so that user input of information is again required to open the drawer and access its contents.

Figure 3:
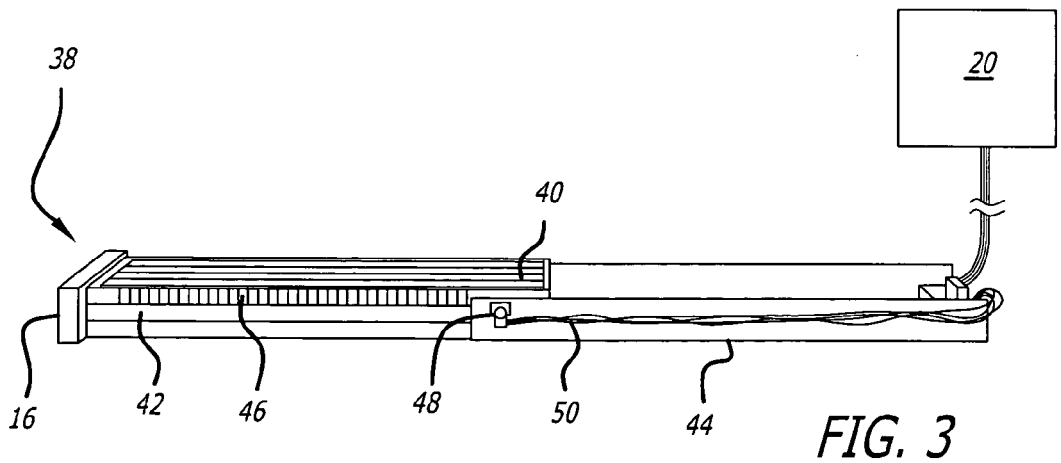
FIG. 3 is a side perspective view of a drawer assembly within the dispensing station of FIG. 1 showing a drawer having multiple storage spaces and a slide control mechanism sensor.

In one embodiment of the invention, the slide control mechanism 19 provides graduated access to progressive rows of storage spaces in a secured-type drawer. As shown in FIG. 3, a drawer assembly 38 comprising a drawer 16 with several transverse rows and longitudinal columns of storage spaces 40 is mounted to a longitudinal rail 42 having a slideable, interlocking connection with a rack 44 mounted to the cabinet 12 (FIG. 2). The drawer assembly is adapted to reside within the cabinet when the drawer is closed and locked. A grid element 46 may be installed along the rail 42 to be read by a drawer sensor 48 mounted on the rack. The drawer sensor is electrically connected via wires 50 to the processor 20 so that the control unit 18 can ascertain how far the drawer has been pulled out of the cabinet based on signals received from the drawer sensor 40. The slide control mechanism is not limited to providing graduated access in fixed increments and, thus, is capable of adapting to irregular drawer configurations.

Another type of drawer that may be employed in the dispensing station 10 is the semi-secured drawer. Typically, control unit 18 allows semi-secured drawers to slide out completely upon user input of required information, such as, for example, when the user logs into the system by entering a personal identifier and password. For convenience, semi-secured drawers may remain unlocked enabling them to be opened and closed repeatedly until an event causing the drawer to be secured occurs, such as, for example, when the user logs off or logs out of the system or when a predetermined amount of time has elapsed.

Figure 4:
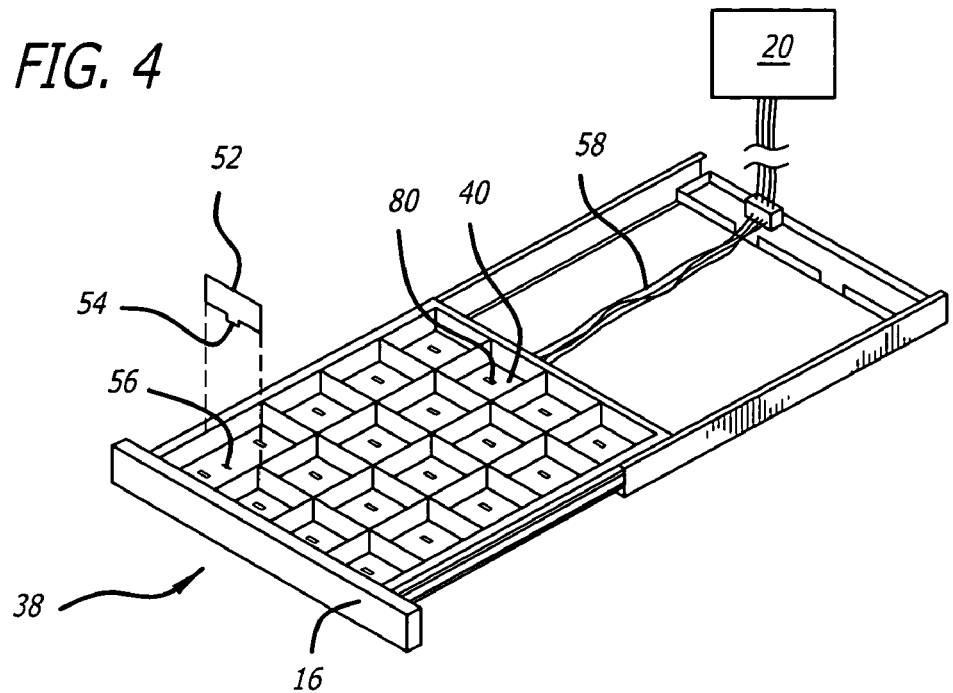
FIG. 4 is a top perspective view of the drawer assembly of FIG. 3 showing removable partitions separating multiple storage spaces.

Referring next to FIG. 4, another embodiment is shown wherein drawer 16 has a plurality of storage spaces 40 separated from one another by vertical divider walls or partitions 52 attached to the floor of the drawer. Only one of the storage spaces and one of the partitions are indicated by reference numerals for clarity and ease of illustration. The storage spaces are shown without lids, although it is contemplated that one or more storage spaces can have a lid hinged to a partition. The lid may serve to further control access or to provide a holder for a label. One or more of the partitions of the drawer is adapted to be removable from the drawer so as to allow reconfiguration of the drawer to suit the user. In the illustrated embodiment, a tab 54 extending from a bottom edge of the removable partitions mates with any number of cooperatively shaped recesses or apertures 56 on the drawer floor. The partitions may be conveniently removed or repositioned simply by lifting them from the floor of the drawer. Those of ordinary skill in the art will appreciate that other means for securing partitions may be employed.

Figure 5:
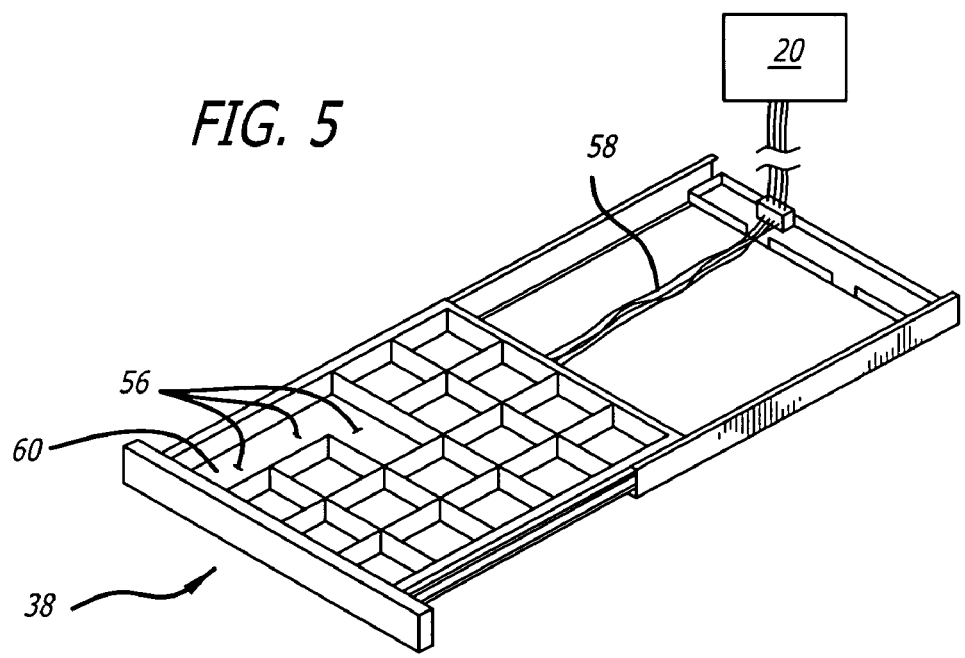
FIG. 5 is a top perspective view of the drawer assembly of FIG. 3 with some partitions removed in order to form an L-shaped storage space.
Figure 6:
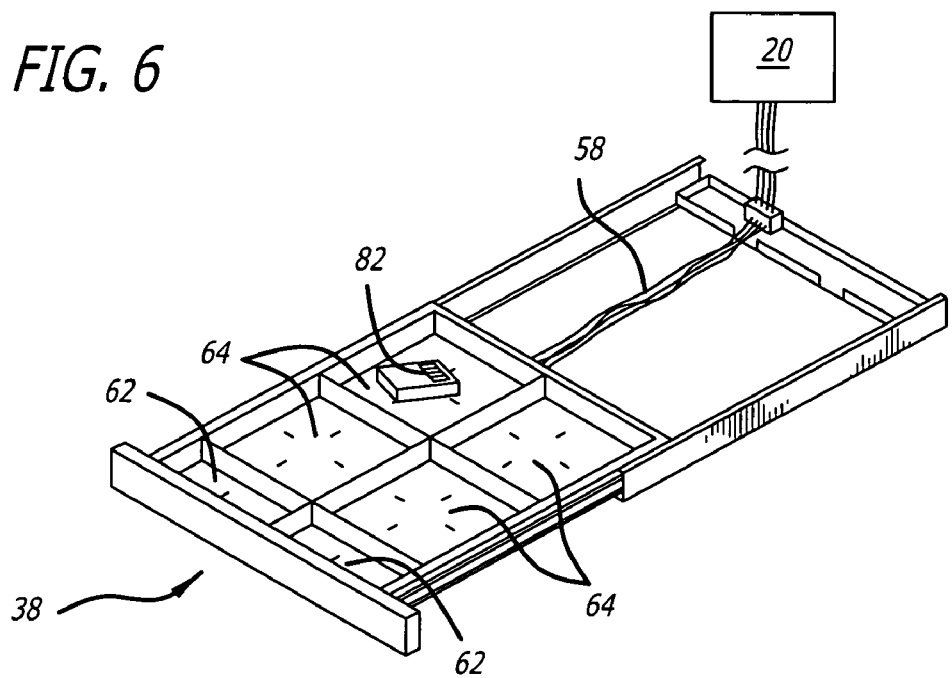
FIG. 6 is a perspective view of the drawer assembly of FIG. 3 with some partitions removed in order to form large storage spaces and further showing a item residing in a storage space.
Figure 7:
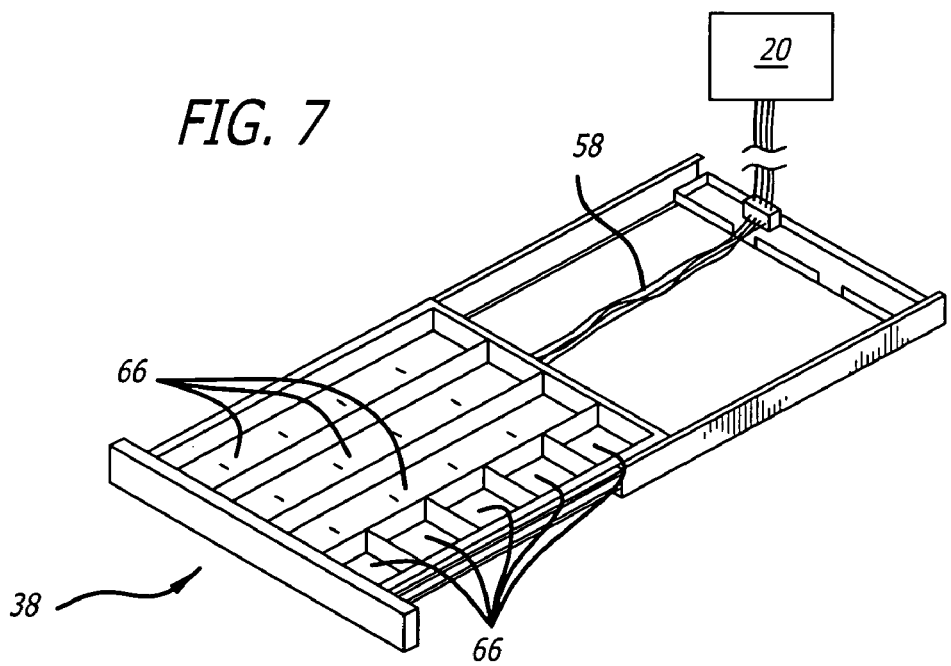
FIG. 7 is a perspective view of the drawer assembly of FIG. 3 with some partitions removed in order to form long and narrow storage spaces oriented longitudinally.
Figure 8:
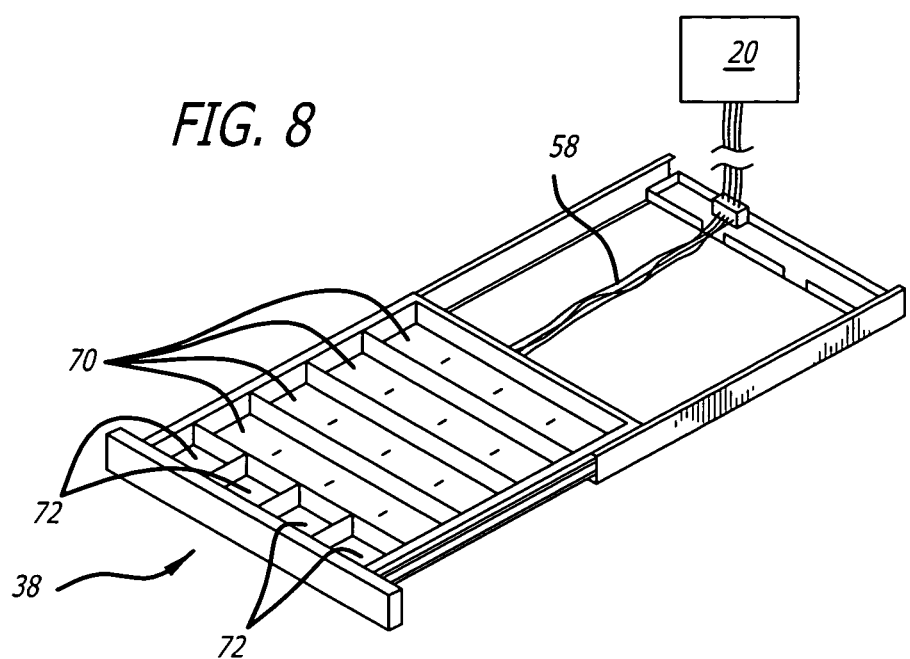
FIG. 8 is a perspective view of the drawer assembly of FIG. 3 with some partitions removed in order to form long and narrow storage spaces oriented transversely.

Referring now to FIGS. 5 through 8, the drawer 16 may be configured to have a combination of storage spaces of different shapes and sizes. FIG. 5 shows a storage space 60 with an L shape, which may be used to hold items having an irregular shape. As shown in FIG. 6, the drawer may be configured with a mix of small storage spaces 62 and larger storage spaces 64. In FIG. 7 there is shown long and narrow storage spaces 66 oriented longitudinally adjacent smaller storage spaces 68. Long and narrow storage spaces 70 may also be oriented transversely adjacent smaller storage spaces 72, as shown in FIG. 8.

Figure 9:
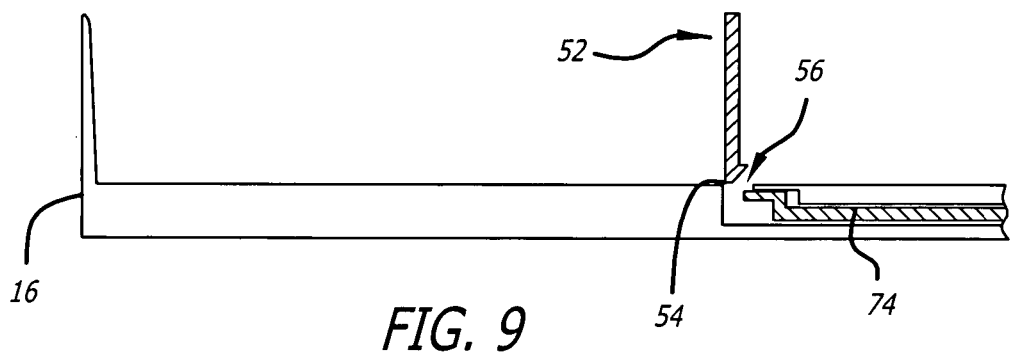
FIG. 9 is a cross-sectional view of a drawer assembly showing a partition disengaged from a latch member within the floor of the drawer assembly.
Figure 10:
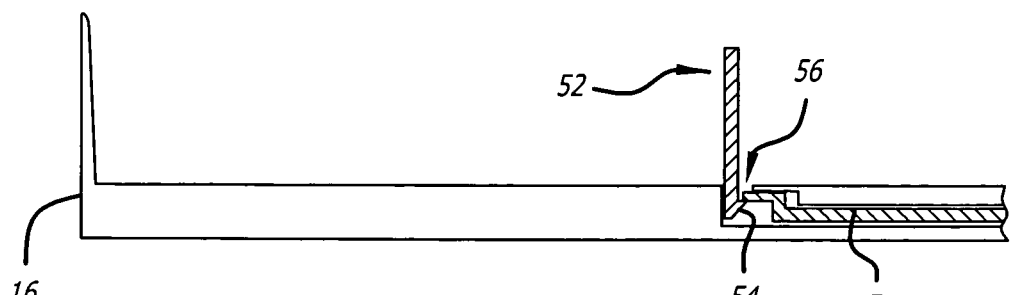
FIG. 10 is a cross-sectional view of the drawer assembly of FIG. 8 showing the partition engaged with the latch member in the floor of the drawer assembly.

In a secured-type drawer that has been unlocked to partially slide open, unauthorized access to items in storage spaces at the rear of the drawer may occur if partitions 52 are not locked in place. Thus, in a further embodiment, to prevent such unauthorized access the partitions may be selectively locked in place by the control unit 18 such that only authorized users may reconfigure drawers by removing or repositioning the partitions. As shown in FIGS. 9 and 10, latch members 74, which are concealed behind the apertures 56 and coupled to muscle wires (not shown) disposed within the drawer floor, engage the tabs 54 so as to lock the partitions in place. Electrical wires 58 connect the processor 20 to muscle wires that are coupled to the latch members. Typically, muscle wires, upon receiving an electrical current based on signals from the processor 20, shrink so as to actuate the latch members so that partitions can be removed or repositioned. This mechanism provides for selective removal of partitions only upon user input of required information.

Before items are stored in a configurable drawer 16, information regarding the layout of the storage spaces of the drawer is provided to the control unit 18 so that the processor of the control unit is aware of the configuration of the drawer so that the proper association can be made between drawer layout and items stored therein can be made. Such storage space-specific information can include the size, quantity, and/or location of the storage spaces 40 in the drawer. Also, information as to which storage space a drug or item is placed for storage is also provided to the control unit, enabling the control unit to ascertain the particular drawer and storage space in which a requested item is stored. Accordingly, when an item is requested by a user, the appropriate drawer can be selected and unlocked by the control unit and the location of the selected storage space can be communicated to the user. When the selected storage space is in a secured-type drawer, the slide control mechanism 19 of the drawer may be operated to allow the drawer to slide open only by the distance necessary to allow graduated access to the selected storage space and prevent access to any other storage spaces to the rear of the selected storage space. Also, when the selected storage space has a locked lid 64, the processor can unlock the lid to allow access to the drug or item stored therein.

In yet a further embodiment, a storage space bar code label 80, such as shown in FIG. 4, may be applied to the storage spaces. Before an item is placed in a storage space for storage, the user scans the storage space bar code using a scanner 28 (FIG. 2) in electronic communication with the control unit 18. As discussed further below, this procedure allows the control unit to identify the storage space in which the item will be stored. Typically, an item bar code label 82, such as shown in FIG. 6, has already been applied to the item by the item manufacturer or supplier. Scanning the item bar code allows the control unit to obtain item-specific information and to associate the storage space with the item to be stored within the storage space. When the same item is subsequently requested by the user either through the keyboard 24 or touch screen 26, the control unit communicates the location of the appropriate storage space to the user and opens the drawer and/or opens the storage space lid as appropriate.

Those skilled in the art will immediately understand that machine-readable identification technologies other than bar codes can be employed, such as radio frequency identification (RFID). RFID tags typically include a microchip attached to a small radio antenna. An RFID tag number can be obtained via an RFID scanner 28' that emits radio waves and receives signals back from an RFID tag within a certain range or distance from the scanner. More sophisticated RFID tags include a microchip that may store information regarding items being stored, eliminating the need for a continuous network connection between the dispensing station 10 and the central computer 34 in order for the control unit 18 to obtain the information about an item. Preferably, the communication range of the RFID scanner 28 is limited so as to avoid unintentionally reading RFID tags on items which are unassociated with the dispensing station, such as items placed on a nearby counter top being carried by personnel past the dispensing station, or stored within an adjacent dispensing station.

Figure 11:
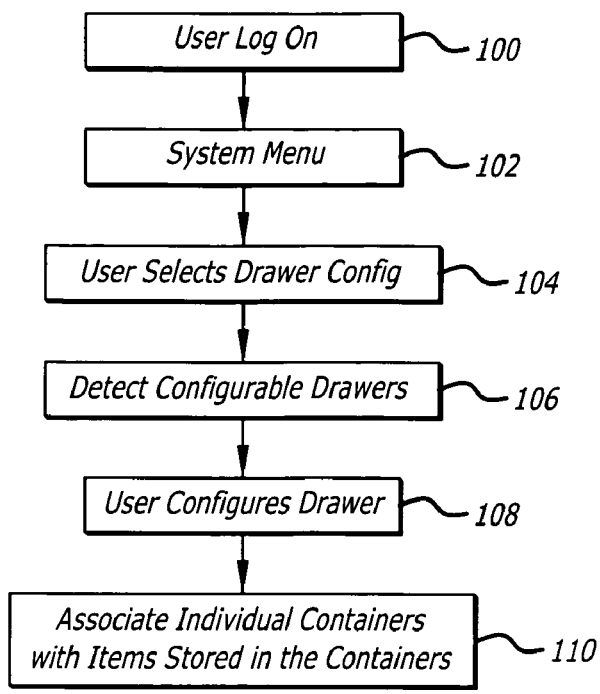
FIG. 11 is a flow diagram of a process for configuring a user interface and control system with the layout of storage spaces in a drawer.

FIG. 11 is a flow diagram depicting one embodiment of a process in accordance with the present invention for storing and tracking usage of items. For convenience of discussion, the process of FIG. 11 will be described in connection with the system 31 of FIG. 2, although it will be appreciated that other systems may be used to implement the method.

Initially, at block 100 of the flow diagram, a user logs on to access a software application associated with the control unit 18 by entering a personal identifier and password via the user interface 22, which may include a biometric scanner in electronic communication with the processor 20. The biometric scanner may be employed alone or in combination with the keyboard 24 and touch screen 26 to authenticate the identity of the user. If the control unit identifies the user as having the appropriate authority to configure the drawers of the dispensing cabinet, a system menu is displayed on the touch screen 26 at block 102.

The system menu has a "Drawer Config" soft key or button for initiating drawer configuration. The "Drawer Config" button is pressed at block 104, and the control unit 18 attempts to detect any drawers capable of being configured at block 106. Such drawers may or may not have been configured previously. Detection may be accomplished through mechanical or electrical connections between the drawer and the processor 20. Alternatively, an RFID tag on the drawer readable by an RFID scanner within the cabinet 12 may be employed for wireless detection. In any case, drawers capable of being configured are listed on the touch screen 26 for selection by the user. When a selected drawer has not been previously configured in the dispensing station 10, a New Drawer Configuration screen is displayed on the touch screen 26, which allows the user to configure the drawers at block 108. Thereafter, the user may store items in the storage spaces at block 110.

Figure 12:
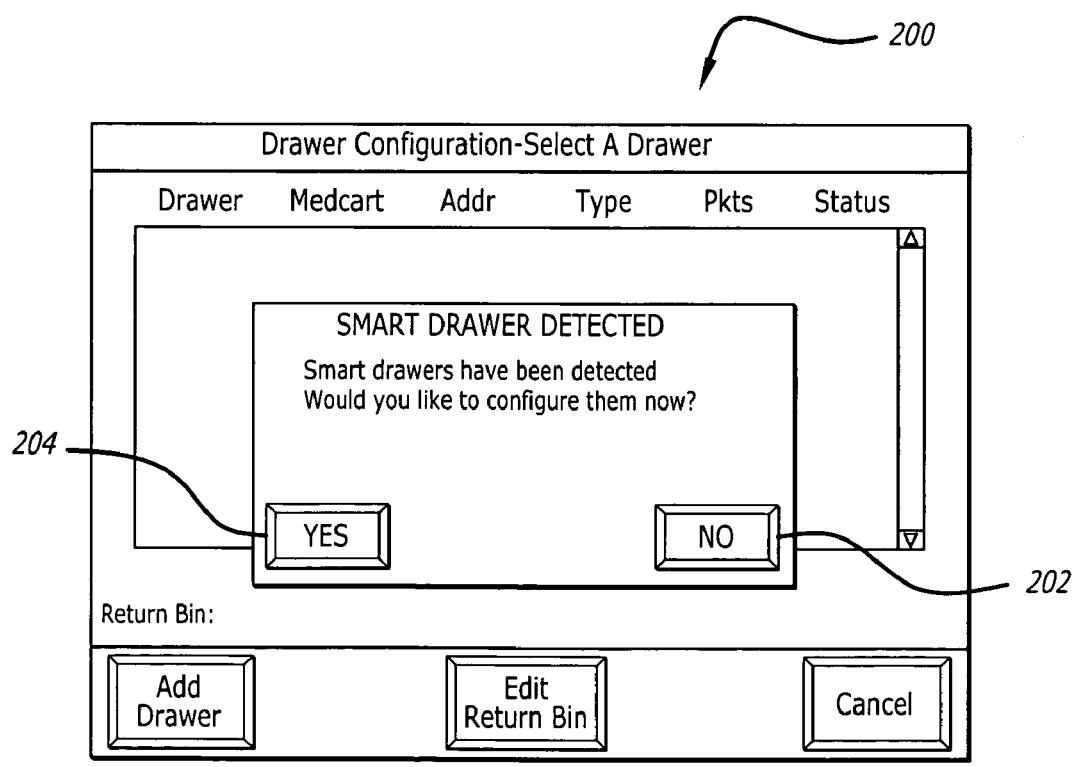
FIG. 12 is a graphical representation of a New Drawer Configuration screen displayed on a touch screen display.

The New Drawer Configuration screen 200, as shown, for example, in FIG. 12, informs the user that configurable drawers, referred to as "smart" drawers in the illustration, have been detected, and inquires whether the user wishes to configure any of them. The screen includes "Yes" and "No" buttons. When the "No" button 202 is pressed, the New Drawer Configuration screen is replaced by the system menu. Preferably, the control unit 18 will not allow items to be stored in a configurable drawer until it receives information regarding the layout of storage spaces in the drawer. When the "Yes" button 204 is pressed, a list of configurable drawers is displayed on the touch screen 26 and the user is prompted to select a drawer. At this point, the user can install partitions 52 on the selected drawer to create storage spaces.

Returning to FIG. 11, after selecting a drawer on the touch screen 26, the user is prompted at block 108 to provide information on the layout of the storage spaces in the selected drawer. Such information may be provided by user via the touch screen 26 displaying a graphical representation of a basic configuration of the selected drawer. As explained in detail below, the basic configuration is modified by the user to create an image representative of one or more storage space locations on the drawer.

Figure 13:
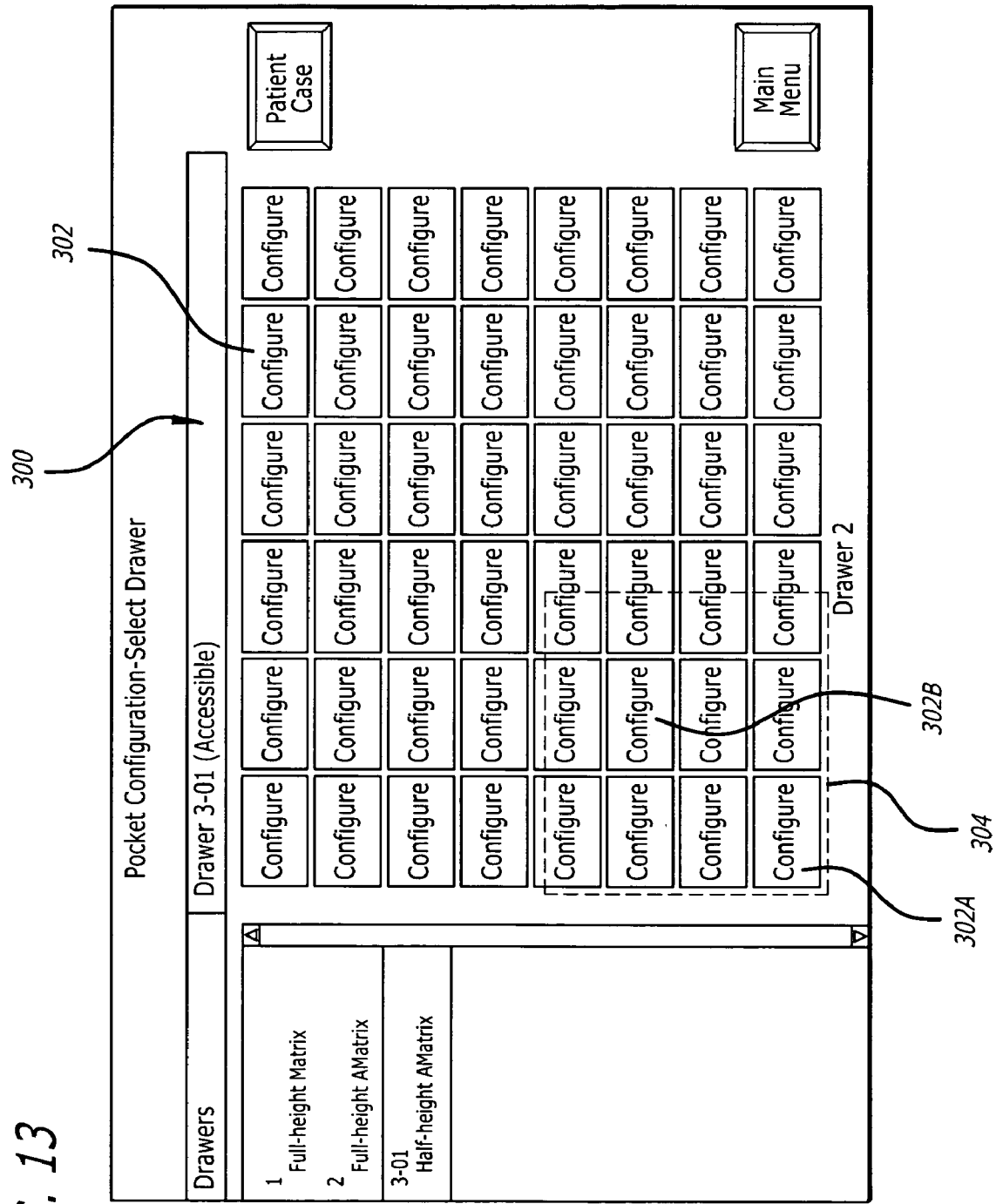
FIG. 13 is a graphical representation of a Basic Configuration screen displayed on a touch screen display showing all potential locations for partitions and all zones of a drawer.

FIG. 13 is a graphical representation of an exemplary basic configuration 300 of a drawer showing all potential locations for partitions and all zones on the drawer. Each zone 302 available for use in defining a storage space is displayed as a non-shaded area and identified with the word "configure." Only one zone is indicated with reference numeral 302 for clarity and ease of illustration. It will be understood that the word "configure" is exemplary, and other terms or symbols may be employed without departing from the scope of the contemplated invention. Similarly, different levels of shading, color, cross-hatching or other graphical device may also be used to indicate which zones of a drawer have been configured.

With the basic configuration 300 as a starting point, the user provides the control unit 18 with storage space-specific information, such as, for example, the quantity, size and/or location of storage spaces in the selected drawer. To do this, the user may assign a rectangular area for each storage space by using the touch screen 26 to select a first zone and a second zone (or any number of other zones).

Figure 14:
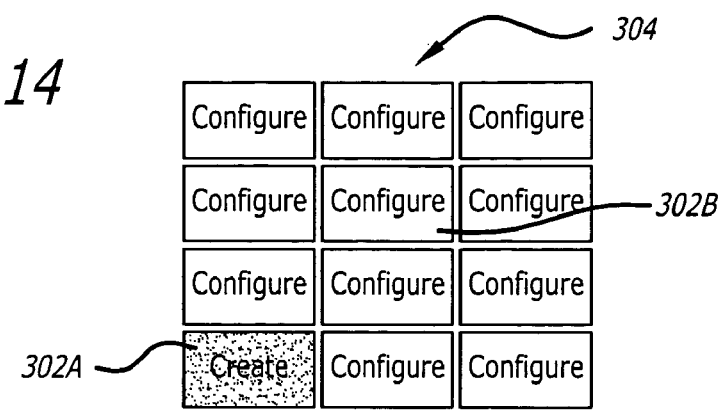
FIG. 14 is a graphical representation of a portion of the Configuration screen displayed on the touch screen display after a first zone is selected from the Basic Configuration screen of FIG. 13.

FIG. 14 shows a section 304 of the basic configuration screen 300 displayed on the touch screen 26. To configure a drawer, the user may, for example, touch a first zone 302A located on the lower left of the basic configuration. The first zone establishes a first corner of a rectangular area and is displayed as a shaded area with the word "create." Of course, other terms or symbols may be employed to identify the selected zone without departing from the scope of the invention.

Figure 15:
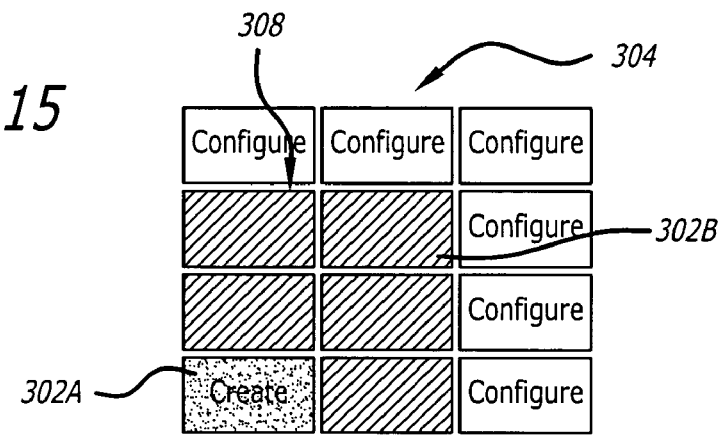
FIG. 15 is a graphical representation of a portion of a Configuration screen displayed on the touch screen display after a second zone is selected from the Configuration screen of FIG. 14.

Referring next to FIG. 15, a user may continue to configure the drawer by touching a second zone 302B that is two zones above and one zone to the right of the first zone 302A. The second zone establishes a second corner that is diagonally opposite from the first corner so as to define a shaded rectangular area 308. If the storage space encompasses only one zone, the user would select the same zone twice, once as the first zone and again as the second zone. The user may continue to touch or select other zones on the touch screen 26 in order to reposition the second corner of the shaded rectangular area.

Figure 16:
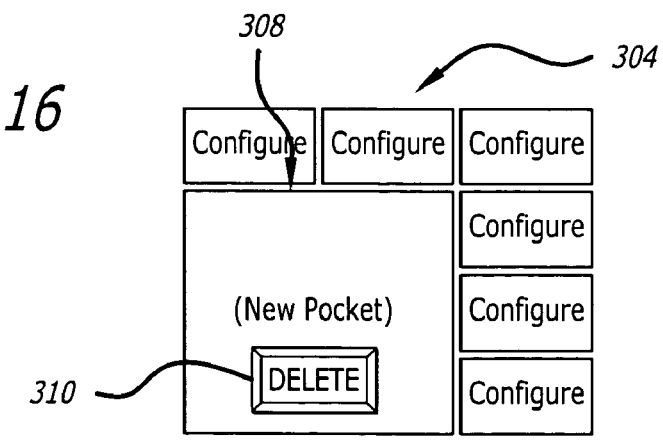
FIG. 16 is a graphical representation of a portion of the Configuration screen displayed on the touch screen display after a Create box is selected from the Configuration screen of FIG. 15.

When the user is satisfied that the shaded rectangular area 308 accurately defines a storage space in the drawer, the user accepts the rectangular area as a storage space definition by touching the word "create" in the first zone 302A on the display screen. Upon touching "create," the storage space definition is stored in memory and the rectangular area 308 is displayed in a lighter shade and labeled with, for example "new pocket," as shown in FIG. 16. A "delete" button 310 is also displayed inside the rectangular area to allow the user to conveniently delete the storage space definition by touching the screen.

Storage space definitions can be stored in a memory storage medium 30 associated with the processor 20 on the dispensing station 10 (FIGS. 1-2). Alternatively or concurrently, storage space definitions can be stored in an RFID tag on a drawer. Thus, when a configured drawer is moved to another dispensing station, the storage space definitions can be communicated automatically to the control unit 18 of that dispensing station via an RFID scanner in the cabinet of the dispensing station.

It will be appreciated that there are other suitable methods that may be used to conveniently provide storage space definitions through the use of the graphical user interface (GUI). For example, after selecting a first zone, the user may be prompted to select an edge of the first zone and to "drag" it across the touch screen. In doing so, the shaded area can be expanded or contracted until it accurately defines a corresponding storage space on the drawer. As a further example, a user may want an L-shaped storage space to accommodate an irregularly shaped item. In this case, the user can be prompted to touch a first zone and any number of adjacent zones as may be required until a shaded area encompassing the selected zones defines the desired L-shaped storage space. This method of individually selecting adjacent zones is also suitable for a drawer that is divided into non-rectangular zones, such as a circular drawer divided into triangular zones.

In yet another embodiment of the present invention (not shown), a non-rectangular storage space can be defined by a series of vertices or corners along its perimeter. In this embodiment, the user is prompted to touch a first corner on the touch screen 26 and any number of additional corners as may be required until a shaded area defined by the corners corresponds to the desired non-rectangular storage space on the drawer.

Returning once again to FIG. 11, after receiving information on the layout of the storage spaces in the drawer, the control unit 18 associates individual storage spaces with items stored in them at block 110. As previously mentioned, bar code labels may be employed as a means of associating storage spaces with items. While the following description refers only to bar codes, it will be understood that other machine-readable identification technologies such as, for example, using RFID tags, may also be employed.

Figure 17:
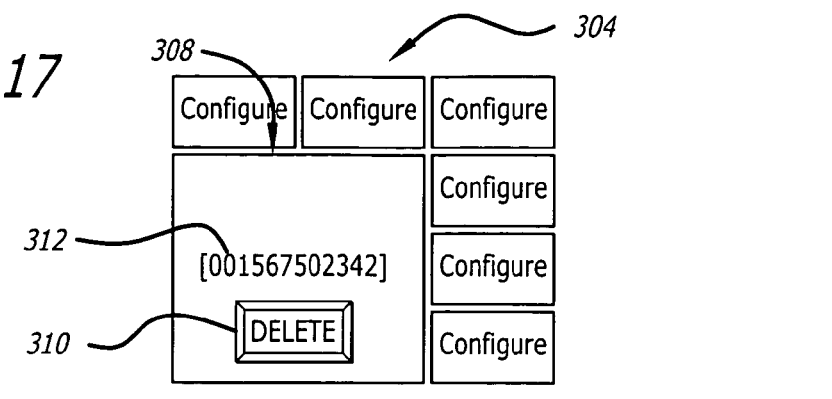
FIG. 17 is a graphical representation of a portion of the Configuration screen displayed on the touch screen display showing an identification number associated with a storage space definition.

At block 110, the user is prompted to identify a storage space on the touch screen 26 and to apply a storage space bar code label 80 (FIG. 4) to that storage space. Afterwards, the user is prompted to scan the storage space bar code label on the selected storage space using a scanner 28 coupled to the control unit 18. The storage space bar code label can be different than bar code labels 82 (FIG. 6) placed on items by the item manufacturer or supplier. The user may be prompted to scan the storage space bar code label a second time so as to detect a potential error in scanning. When the two scans match, the corresponding rectangular area on the touch screen is labeled with an identification number or code 312 derived from the bar code label, as shown in FIG. 17. Preferably, although not necessarily, this step is performed for every storage space before items are stored in the drawer. Thereafter, any storage space in the drawer can be identified by the control unit when the user scans its storage space bar code label.

After storage space bar code labels 80 have been affixed to the storage spaces and scanned, the user may begin to store items in any of the storage spaces. To associate a storage space with a particular group of items, the user scans the storage space bar code label 80 of a selected storage space in which a group of items will be stored, then scans the item bar code label 82 on every item placed in the selected storage space. By scanning the bar code label 82 on each item, the control unit 18 can track the quantity of items being placed into the selected storage space. The user may scan the storage space bar code label again to indicate that the final item was placed in the selected storage space. Alternatively, the user may be prompted to enter a numerical quantity via the keyboard 24, or to take some other action specifying that loading of the drawer storage space is complete.

Preferably, item bar code labels 82 contain item-specific information related to the items to be stored in the storage spaces, such as, for example, an item description and expiration date, so that the information need not be manually provided to the control unit 18 via the keyboard 24 prior to storing the items in the dispensing station 10. The information can be stored by pharmacy staff in a storage medium 36 associated with a central computer 34. Information may then be retrieved by the dispensing station 10 from the central computer or storage medium 36 via a wired or wireless network 32. Alternatively, the information can be stored by personnel in a storage medium 30, such as a hard disc or optical disc, associated with the dispensing station processor 20. In any case, the control unit can obtain information regarding an item when the item bar code label is scanned.

In an alternative embodiment of the present invention, the storage space bar code labels 80 that are applied to the storage space are already associated with information regarding the items to be stored in the storage space, so that the user storing items in the dispensing station need not scan the item bar code labels 82 on each item being stored. For example, items can be grouped or batched together by an individual at a pharmacy, at which time he or she generates a storage space bar code label 80 having item-specific information, such as, for example, a batch identifier, an expiration date, and other information regarding the items to be loaded into the storage spaces. Afterwards, when placing the batch of items in a storage space in the dispensing station 10, the user affixes the storage space bar code label onto the storage space and scans the storage space bar code label to allow the control unit 18 to obtain the item-specific information automatically.

Since individual storage spaces are associated with items stored in them, when an item is requested by the user, the storage space location can be displayed and, if necessary, the appropriate drawer can be unlocked so as to allow the user to find and remove the item. However, the user may already know the storage space location of the requested item in a drawer that is already open. In this case, rather than identifying the item in advance, it is desirable to allow immediate removal of a desired item without having to identify the item via the keyboard 24 prior to removal. Once the item is removed from its storage space, the item can be quickly identified using the touch screen 26 or a bar code scanner 28.

An intuitive and efficient workflow is achieved by using the touch screen or scanner as described below in connection with FIG. 20.

Figure 18:
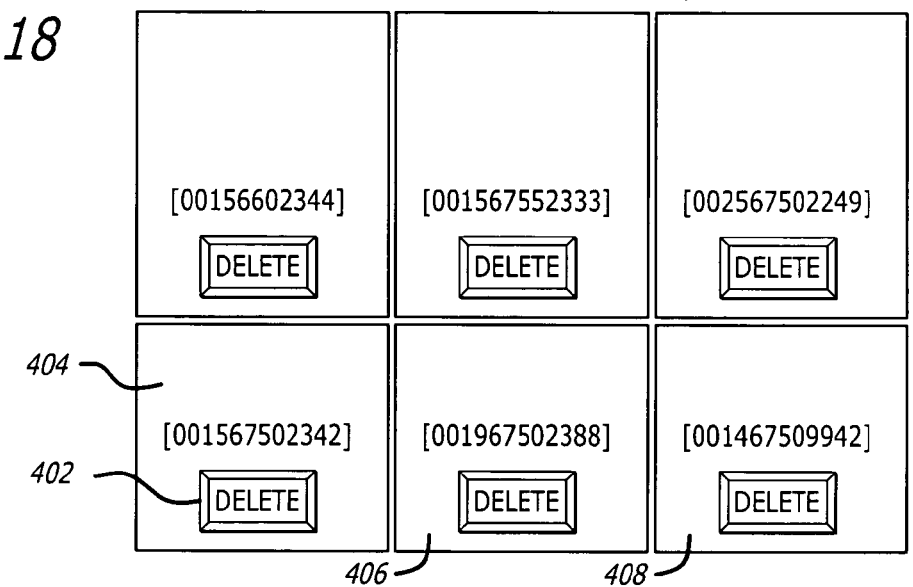
FIG. 18 is a graphical representation of a portion of the Configuration screen displayed on the touch screen display showing Delete buttons for each of six storage space definitions.

A drawer may, of course, be configured again. As previously mentioned, the control unit at block 106 attempts to detect any drawers that have been previously configured in the dispensing station so as to allow the user to select any such drawer for reconfiguring. The process of reconfiguring a drawer is similar to the first-time configuration process described above in connection with FIGS. 11-16. Rather than displaying the basic configuration 300 of the drawer as shown in FIG. 13, the touch screen displays the current configuration 400 of the drawer as shown, for example, in FIG. 18. From the touch screen 26, the user can select or touch "delete" buttons 402 within the graphical storage space definitions that correspond to the portion of the drawer that the user wants to reconfigure. Thus, the user avoids having to redefine storage spaces that have not changed.

Figure 19:
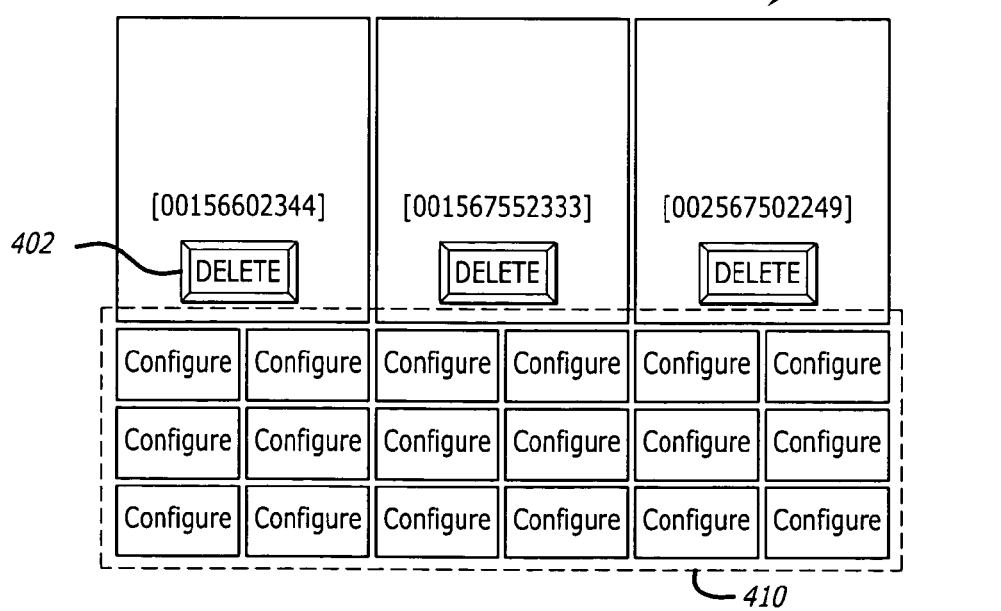
FIG. 19. is a graphical representation of a portion of the Configuration screen displayed on the touch screen display after three Delete buttons were selected from the Configuration screen of FIG. 18.

Referring now to FIG. 19, upon selecting "delete" in the three bottom most graphical storage spaces definitions 404, 406, 408 (FIG. 18), all the zones within the corresponding area 410 are displayed and labeled as "configure." At this point, one or more new storage spaces can be defined by the user as previously described above in connection with FIGS. 14-16.

Since the storage space definitions are stored, for example, in a storage medium 30 associated with the dispensing station processor 20 or in an RFID tag on the drawer, a virtual layout of storage spaces in the drawers can be displayed on the touch screen 26. The virtual layout can be, for example, but not limited to, a plan view, perspective view or other graphical representation of the drawer. Display of the virtual layout on the touch screen 26 eliminates the need to have an array of individual lights and switches mounted adjacent the storage spaces for indicating to the user the location of an item and for recording which storage space an item was removed.

Figure 20:
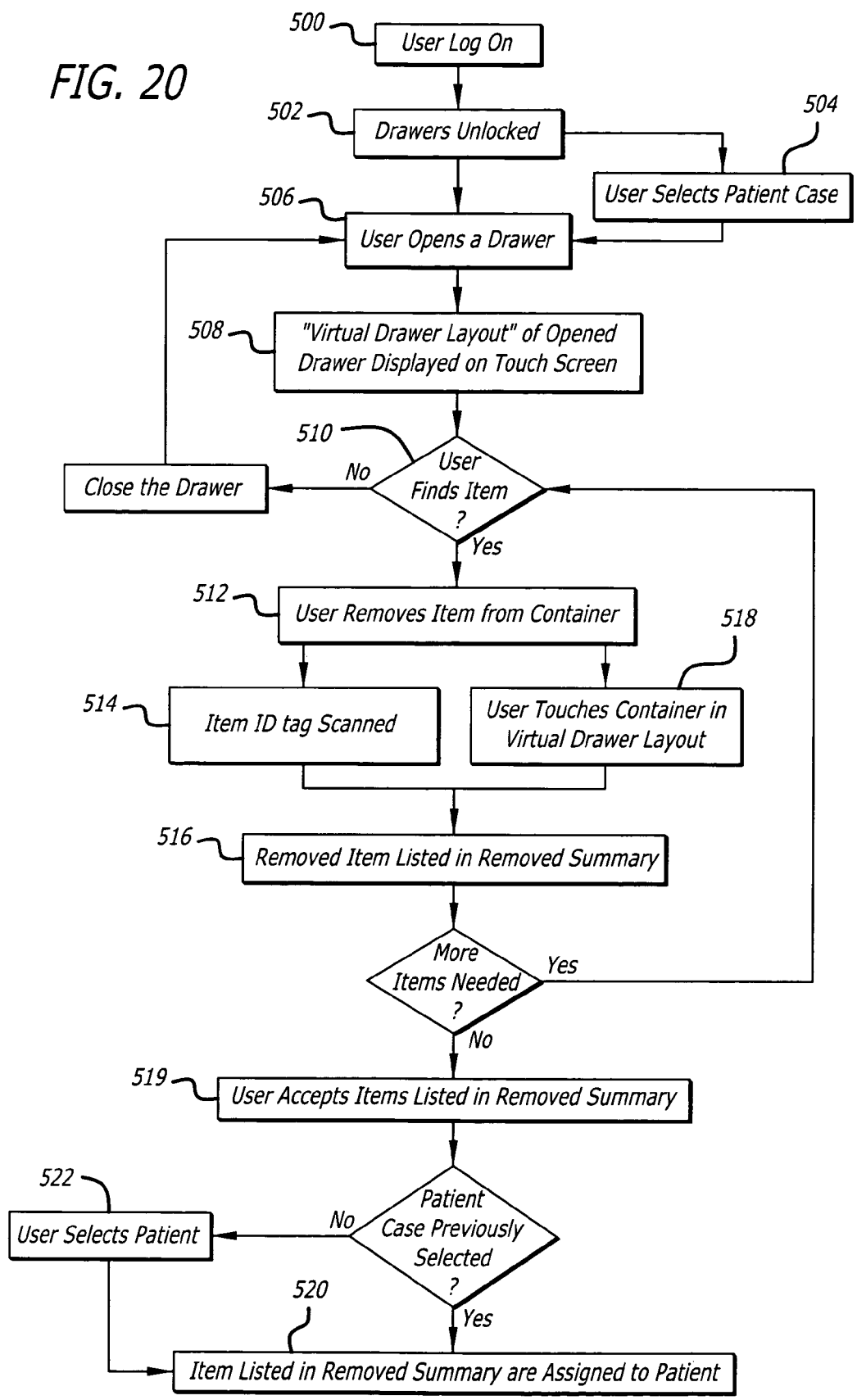
FIG. 20 is a flow diagram of a process for immediate removal of an item from a drawer.

FIG. 20 shows a flow diagram of a process for removing an item from a drawer in a dispensing station in accordance with another embodiment of the present invention. Initially a user logs on at block 500 to configure the drawers of the cabinet. When the control unit recognizes the user as having the appropriate authority, one or more drawers are unlocked at block 502. As described further below, the user may continue by selecting a patient case to which subsequently removed items will be assigned at block 504.

Figure 21:
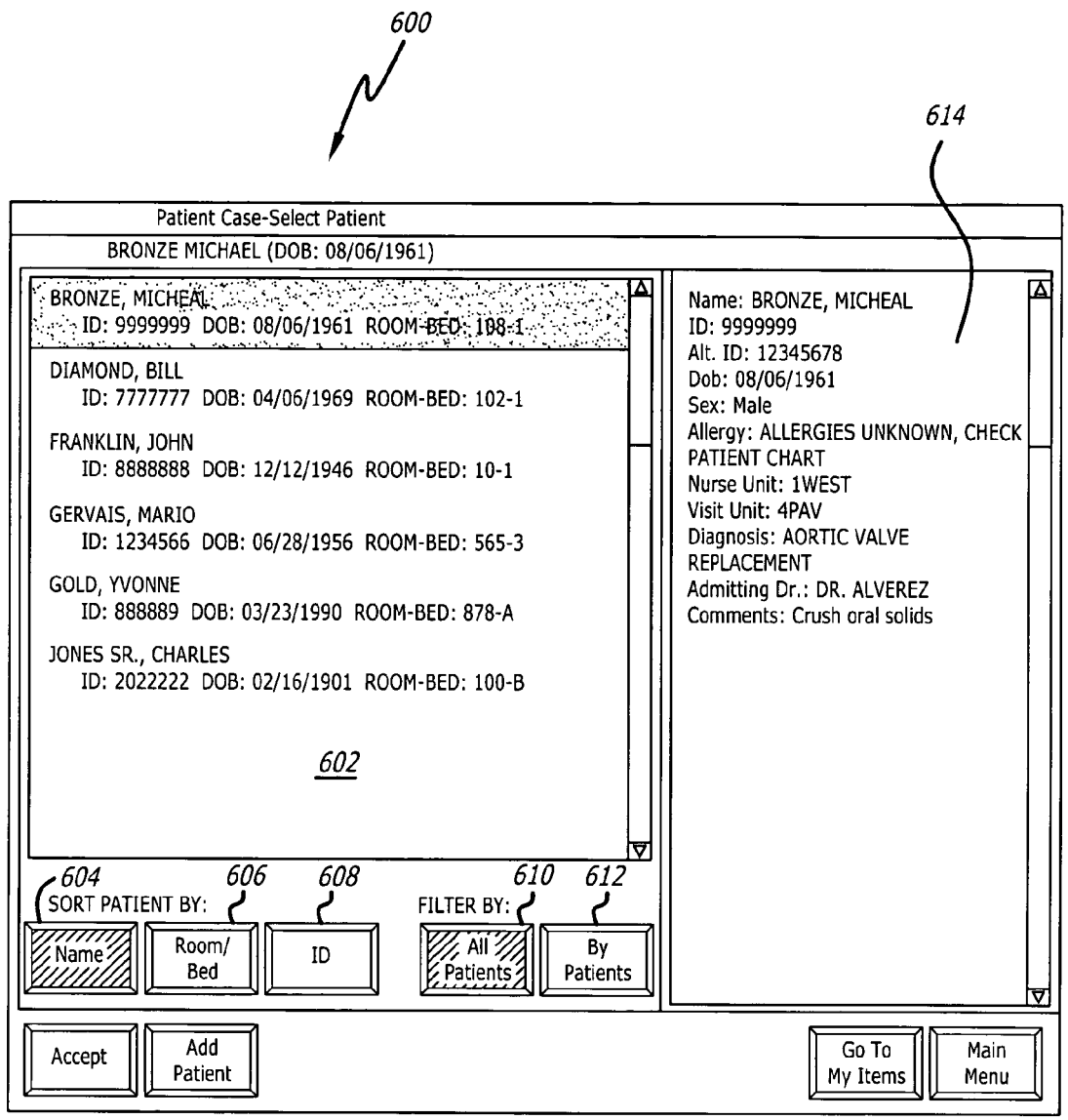
FIG. 21 is a graphical representation of a Select Patient screen showing patient demographic information of a patient.

At block 504, a Select Patient Screen 600, as shown, for example in FIG. 21, is displayed on the touch screen 26. A list of patients 602 is shown on the left side of the Select Patient Screen. Below the list are buttons 604, 606, 608 for sorting the list of patients by name, room/bed, or identification code. To allow for more rapid selection, the list of patients may be shortened by limiting or filtering the list so that only the patients under the care of the logged on user are displayed. Accordingly, there are additional buttons 610, 612 labeled "All Patients" and "My Patients" for listing either all patients or patients assigned to the logged on user, respectively.

The user may quickly select a patient by selecting the name of the patient on the list displayed on the touch screen. Upon selecting a name, the patient's demographic information 614 is displayed on the right side of the screen. The demographic information 614, for example, comprises date of birth, gender, and other identifying information so as to allow the user to confirm that the correct patient is selected. Information on known allergies, diagnosis, and other comments, which can later aid the user in the proper selection of items from the dispensing station 10, may also be included in the patient demographic.

Returning to FIG. 20, after selecting a patient case at block 504, the user may open any unlocked drawer at block 506 to access an item in that drawer. Alternatively, the user may proceed from block 502 to open an unlocked drawer without previously selecting a patient case. Preferably, when the user fails to open any drawers or closes all the unlocked drawers, a reminder is displayed on the touch screen 26, such as: "To begin removing please pull open the drawer." After opening a drawer, a virtual layout of the storage spaces in the opened drawer is displayed on the touch screen at block 508.

Figure 22:
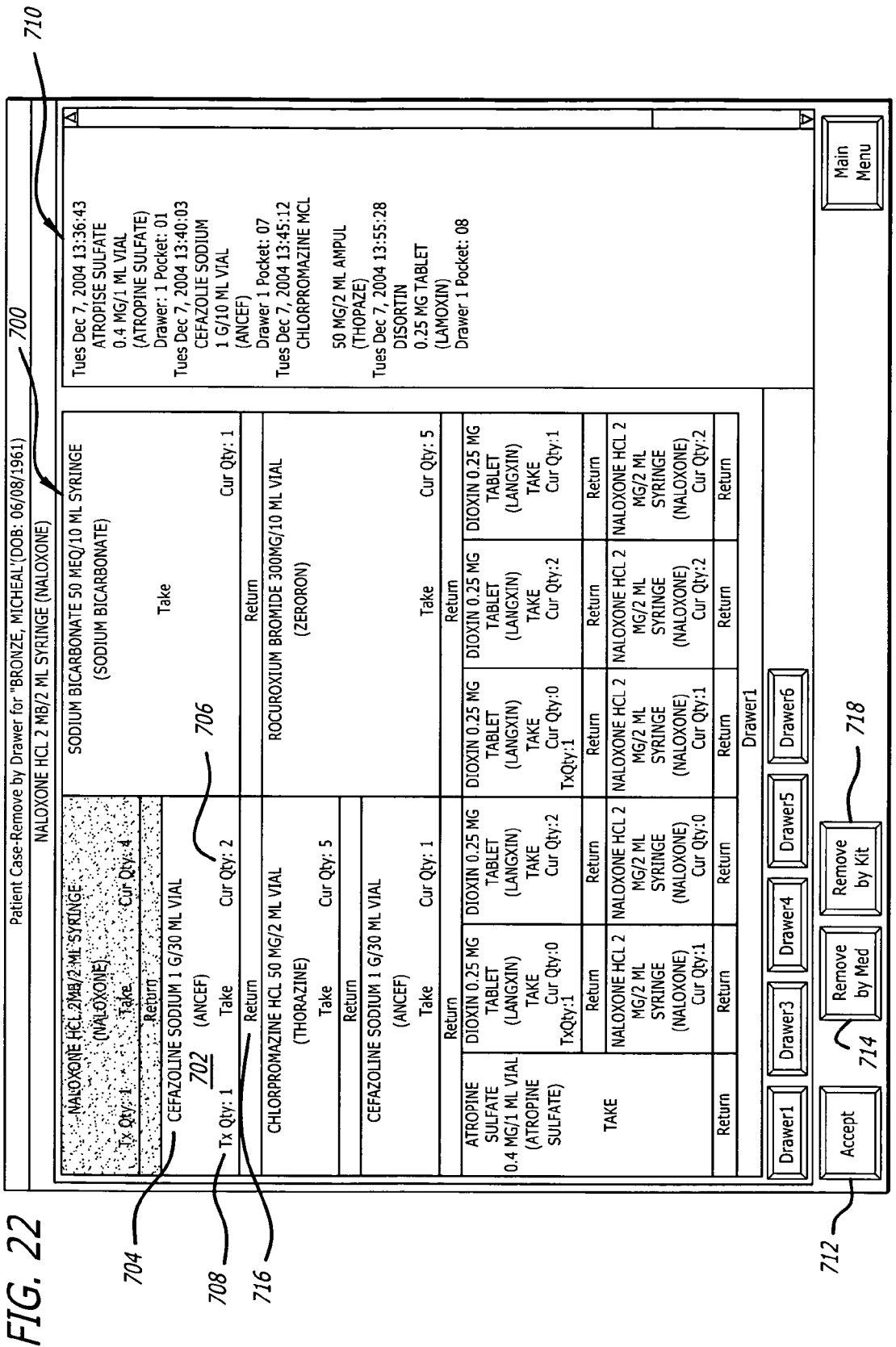
FIG. 22 is a graphical representation of a virtual layout showing virtual storage spaces with descriptions of the items stored in corresponding storage spaces.

As shown in FIG. 22, for example, a virtual layout 700 includes virtual storage spaces 702 that are rectangular areas representing the relative locations of the storage spaces within the opened drawer. Descriptions 704 of stored items, such as CHLORPROMAZINE HCL 50 MG/2 ML AMPUL (THORAZINE), are displayed within the respective virtual storage spaces 702 on the touch screen 26. The descriptions help the user find the item the user needs. Preferably, the current quantity 706 of items is also displayed to help the user identify accounting discrepancies. A transaction quantity 708 may also be displayed within the virtual storage spaces. The transaction quantity increments by the number of units taken and serves as a convenient reminder to the user of the total number of items that were taken from a particular storage space. When a needed item is not in the drawer, the user can close the drawer and open another unlocked drawer. At this point, the virtual layout 700 and descriptions 704 on the touch screen are updated to reflect the newly opened drawer.

In another embodiment of the present invention, more than one drawer can be opened or pulled out simultaneously. In this embodiment, more than one virtual layout 700 can be displayed on the touch screen 26, although typically, only one virtual layout is active for recording a transaction. Generally, the active virtual layout is displayed in the foreground, and any inactive virtual layouts are displayed in the background such that they are partially obscured by the active virtual layout. Preferably, the active virtual layout corresponds to the opened drawer that is pulled out the furthest and/or the opened drawer that is obstructing other opened drawers beneath it. Accordingly, the control unit 18 monitors the extent to which each drawer is pulled out to determine which virtual layout to make active on the display screen.

Referring again to FIG. 20, after the needed item is found by the user at block 510, the user may simply remove the item from the storage space at block 512. After removing an item, the user at block 514 may scan the bar code label 82 on the removed item in order to record the transaction. At this point, the current quantity 706 (FIG. 22) displayed within the virtual storage space 702 decreases by one unit of measure. If two items were removed, the user may scan the bar code label on both items and the current quantity displayed decreases by two units of measure. A cumulative transaction list or a removed summary 710 is conveniently displayed adjacent the virtual layout 700. Upon scanning the item bar code label 82, the item description, storage space location, and date and time of removal are added to the removed summary at block 516. The removed summary serves as a convenient reminder to the user that an item was already removed and reduces the possibility of unnecessarily removing, and possibly wasting or discarding, additional items.

In an alternative embodiment, instead of scanning an item bar code label 82 in order to record the transaction, the user may, at block 114, select the corresponding virtual storage space 702 on the touch screen 26. When the current quantity in the storage space is greater than zero, the word "Take" is displayed in the virtual storage space to indicate that selecting or touching the virtual storage space will record a transaction.

Upon selecting the virtual storage space by touching its displayed image, the removed summary 710, the current quantity 706 and the transaction quantity 708 displayed within the virtual storage space are updated.

After the user scans the item bar code label or selects the appropriate virtual storage space, the user can accept all the items listed in the removed summary 710 at Block 519. Typically, an "Accept" button 712 (FIG. 22) is displayed near the bottom of the touch screen 26. Upon pressing the "Accept" button, the control unit 18 assigns usage of all the items listed on the removed summary to the previously selected patient case. When a patient case has not been previously selected at block 504, the user is prompted to select a patient at block 522, after which, usage of all the items listed on the removed summary 710 is assigned to the selected patient case.

Figure 23:
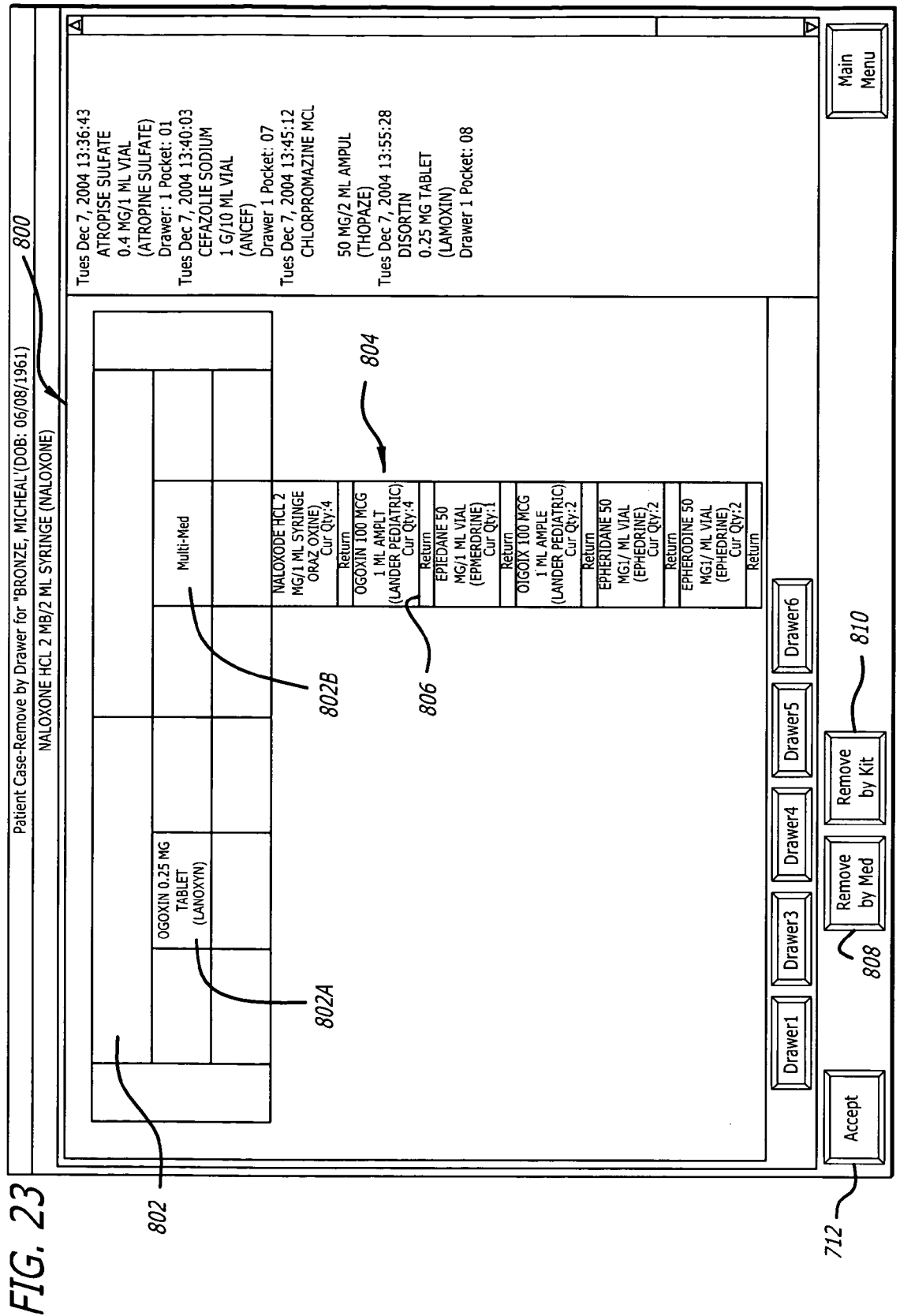
FIG. 23 is a graphical representation of a virtual layout showing a partial front view of a dispensing station with descriptions of the items stored in corresponding drawers.

Another embodiment of the present invention may include a dispensing station 10 with narrow drawers. In this case, a virtual layout different than that shown in FIG. 22 may be displayed on the touch screen 26. For example, as shown in FIG. 23, a virtual layout 800 can show a front view of the cabinet 12 illustrating the relative location of the drawers 16 of the cabinet. In this virtual layout, each rectangle represents a virtual drawer 802. Only one virtual drawer is indicated by reference numeral 802 for clarity and ease of illustration. When a drawer contains items having the same description, such as in virtual drawer 802A, the item description is displayed within the respective virtual drawer. To record a transaction, the user may simply touch a virtual drawer having an item description.

In a further embodiment, one or more of the drawers can be partitioned into a single column of multiple storage spaces with each storage space storing a different type of item. In this case, "Multi-Med" is displayed in the corresponding virtual drawer, such as shown in virtual drawer 802B. When the user touches the word "Multi-Med" on the touch screen or physically opens a Multi-Med drawer, a column of virtual storage spaces 804 is displayed directly beneath the virtual drawer. The descriptions of the items stored in the storage spaces, including the transaction quantity, and current quantity, are displayed within the virtual storage spaces. To record a transaction, the user may simply touch any of the virtual storage spaces displayed on the touch screen 26.

In yet a further embodiment of the present invention, a "Return" button 716, 806 is displayed within each of the virtual storage spaces described in connection with FIGS. 22 and 23. By pressing the "Return" button on a particular storage space, the user can quickly record the return of an item to that storage space.

In some situations, such as before a medical procedure, the user has in mind a long list of items that need to be removed from a dispensing station for later use during the medical procedure. Generally, the items are stored in several different drawers in the dispensing station. As such, it is convenient and more efficient for the user to create a list of items to be removed and then proceed to remove the items from the drawer. By removing the items based on a predefined list, the control unit 18 can order removal of the items one drawer at a time, which saves time since the user will not have to open and close a drawer more than once. Thus, in another embodiment of the present invention, a graphical user interface can be employed to enable the user to conveniently and rapidly create such a list that will subsequently guide the user in the order of removal of items from the dispensing station.

Figure 24:
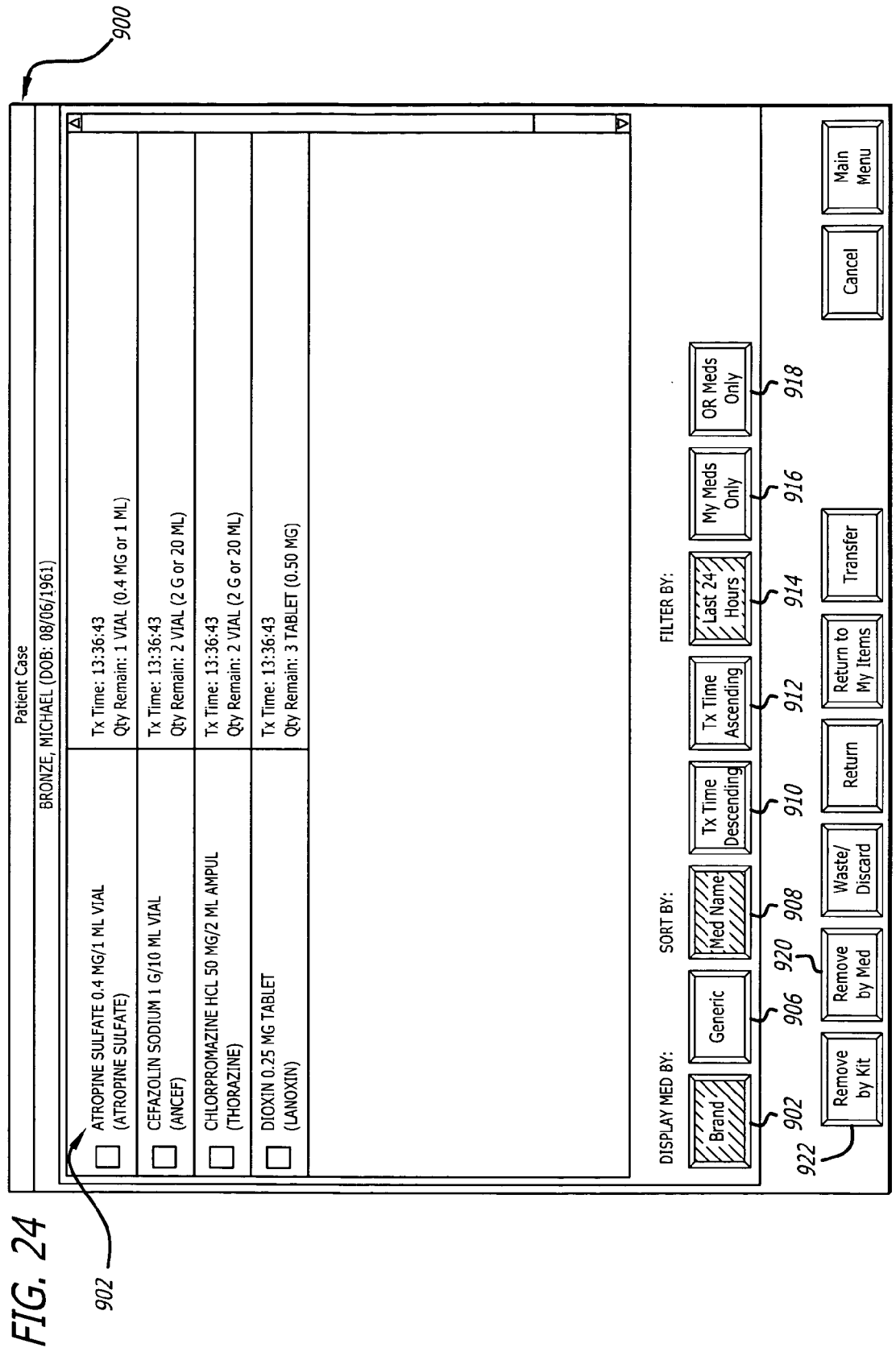
FIG. 24 is a graphical representation of a Patient Case main screen showing buttons for selecting methods for removing items.

A Patient Case Main screen 900 is shown in FIG. 24 that includes a list of items 902 that have been previously assigned to the patient. The list of items can be displayed using the brand name or generic name of the items by selecting either a "Brand" button 904 or a "Generic" button 906, respectively. Also, the list can be sorted according to item name, descending transaction time, or ascending transaction time via a "Med Name" button 908, "Tx Time Descending" button 910, and "Tx Time Ascending" button 912, respectively. Additionally, a "Last 24 Hours" button 914, a "My Meds Only" button 916, and a "OR Meds Only" button 136 are provided to filter or shorten the list 902 either to items assigned within the last 24 hours, items assigned by the user, or items used in the operating room, respectively. At the bottom of the screen 900 is a "Remove by Med" button 920, which allows the user to create a list of items to be removed from the dispensing station.

Figure 25:
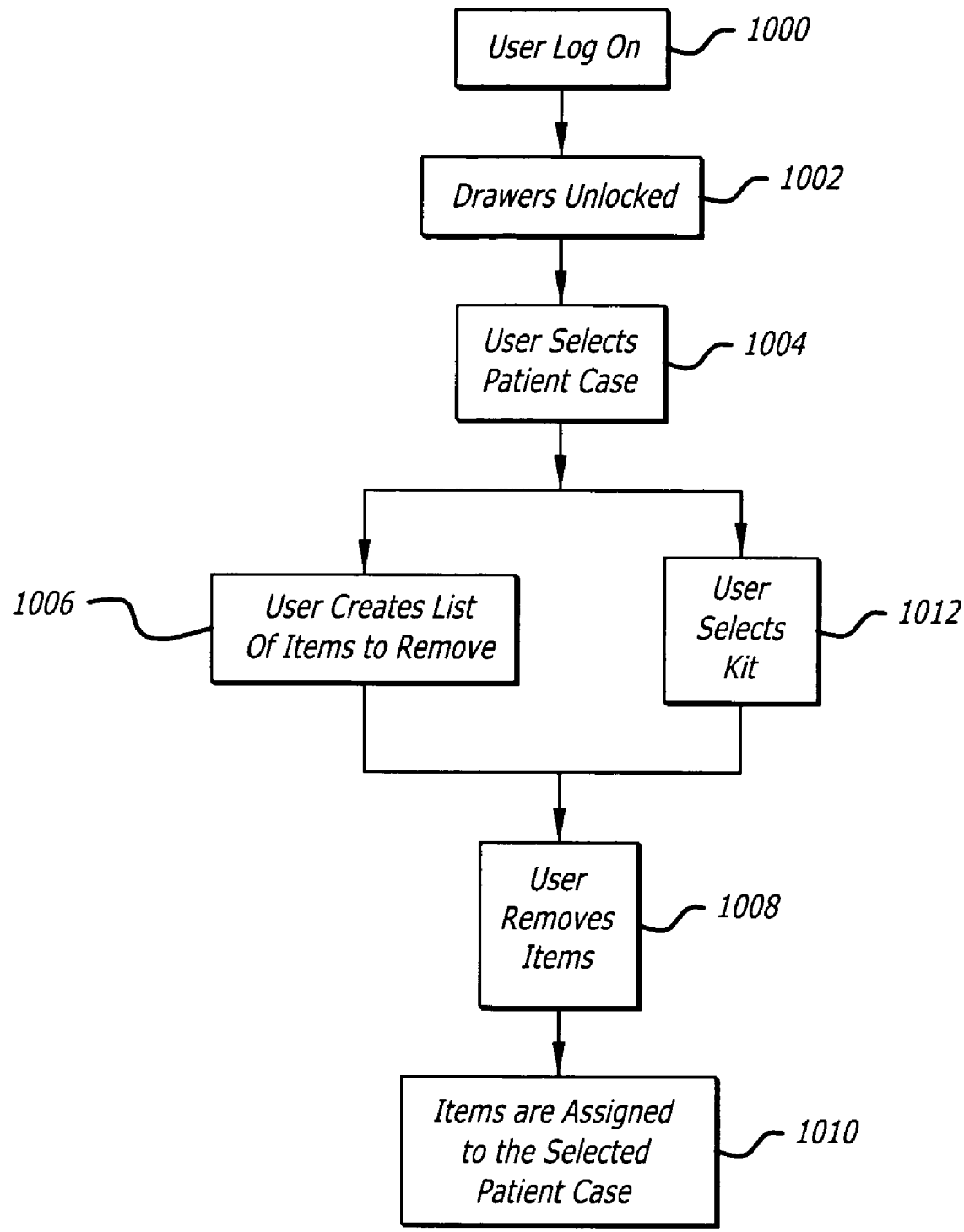
FIG. 25 is a flow diagram of a process for removing items from drawers based on predefined lists.

Referring now to FIG. 25, a flow diagram illustrating a process for removing an item from a drawer in accordance with another embodiment of the present invention is shown. Initially, a user logs on to the system 31 at block 1000 so as to unlock the dispensing station drawers at block 1002. After selecting a patient case at block 1004, the user may either create a list or select a predefined list of items to be removed from the dispensing station. Upon pressing the "Remove by Med" button 920 (FIG. 24), the user is prompted at block 1006 to create a list of items for removal. To facilitate rapid creation of the list, a Medication Selection screen is displayed on the touch screen 26.

Figure 26:
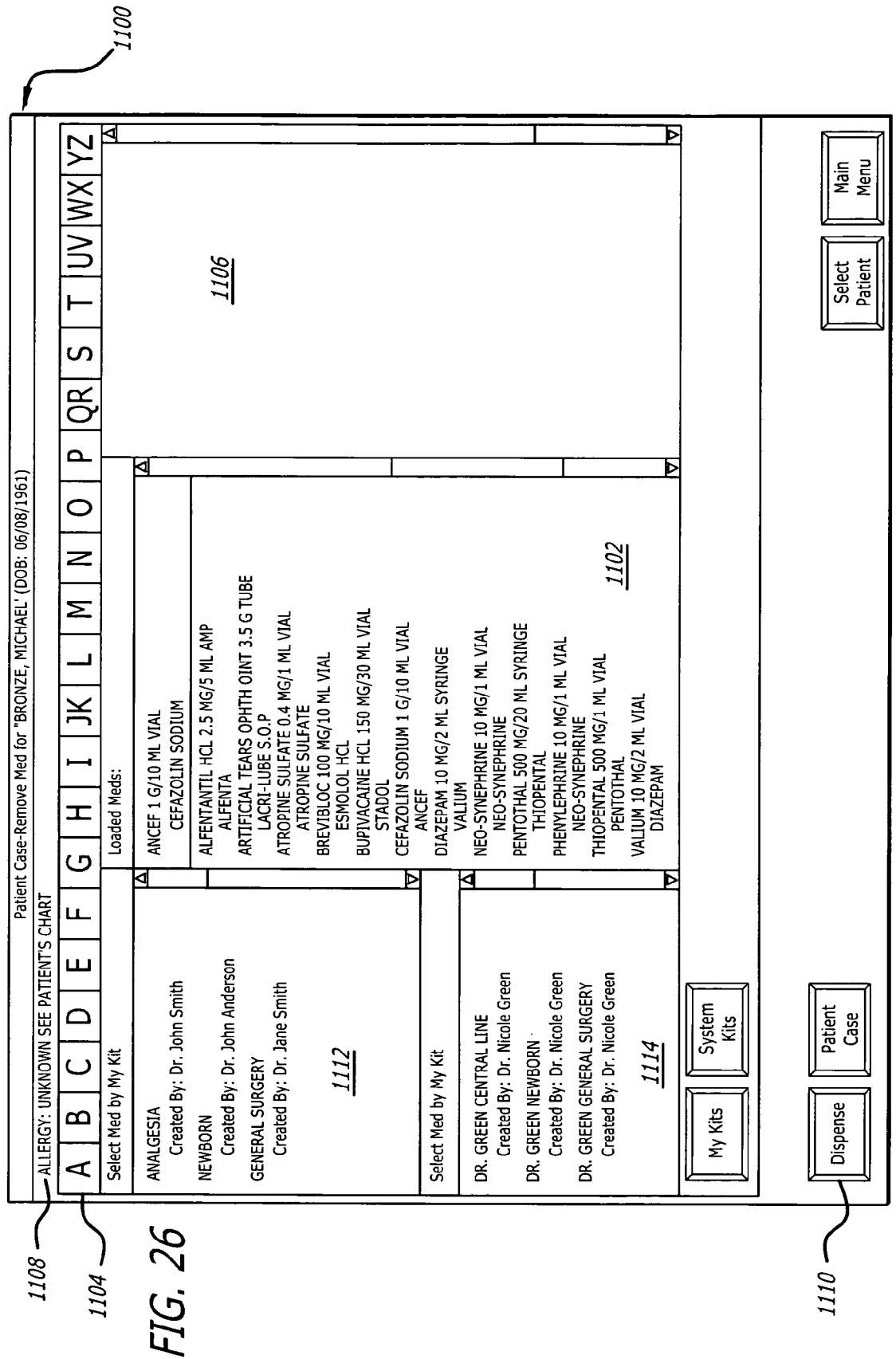
FIG. 26 is a graphical representation of a Medication Selection screen showing a list of kits, an alphabetical list of items in a dispensing station, and a summary of items selected for removal.

As shown in FIG. 26, for example, the Medication Selection screen 1100 includes a center panel display containing a list 1102 of items stored or loaded in the dispensing station 10. The list of stored or loaded items may be sorted and displayed in alphabetical order, although other orders may be displayed depending on the setup of the screen and/or the user's needs. Above the list 1102 are a row of buttons 1104 labeled with letters of the alphabet to allow the user to shorten the list to items with names beginning with a selected letter. Alternatively, the buttons 1104 may be used to rapidly display to the portion of the list where items begin with a selected letter.

To select an item at block 1006 (FIG. 25), the user simply selects the name of the item on the list 1102 displayed on the touch screen 26. Preferably, the default quantity is one unit of measure. For additional quantities of the same item, the user may simply select the name of the item again so as to avoid having to enter a quantity via the keyboard 24. The keyboard, however, may be used to change the quantity or to enter a numerical quantity directly. Selected items are shown in a cumulative list or summary 1106. As a reminder to the user, the patient's name, date of birth, and allergies are shown in a header bar 1108 at the top of the Medication Selection screen 1100. Other information may be displayed as well, which may be predetermined by the institution, or made available through an appropriate setup process initiated by the user. A "Dispense" button 1110 at the bottom of the screen is provided to allow the user to indicate that the final item has been selected and that the list of items for removal is complete. After the user finishes creating the list at block 1006, the list is reorganized by the processor 20 such that the items are grouped according to the dispensing station drawer in which they are stored. Thereafter, the user may proceed to remove the items at block 1008.

Figure 27:
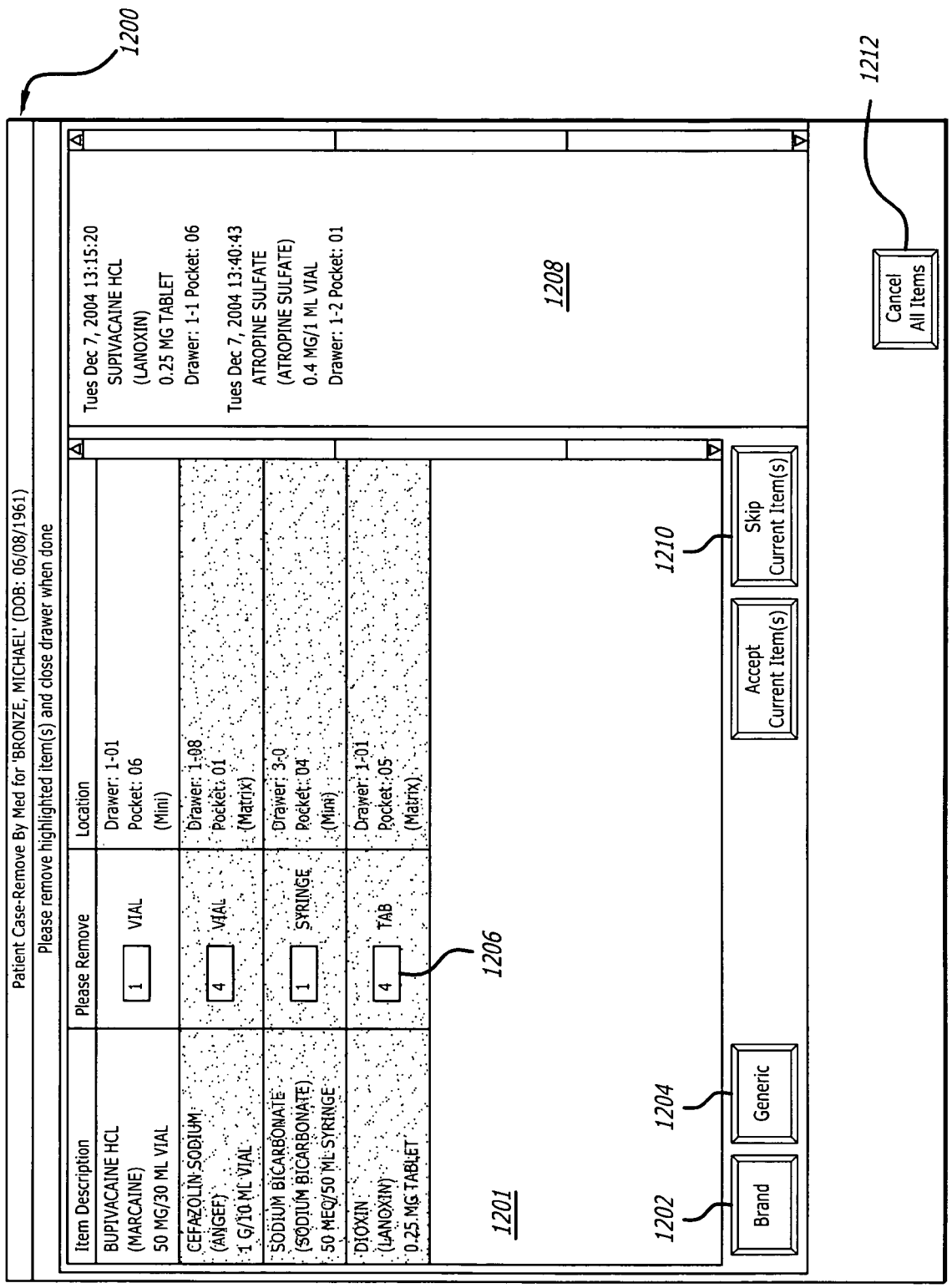
FIG. 27 is a graphical representation of a Guided Removal screen showing items for removal organized by drawer and storage space locations.

A Guided Removal screen 1200 is shown in FIG. 27. This screen includes, among other information, a list of items identified at block 1008 (FIG. 25) for removal. The items to be removed are listed in a panel 1201, with columns displaying, for example, the item description, removal quantity, and drawer/storage space identifier or location of the item in the dispensing station. To aid the user in recognizing items, the brand name or generic name of the items can be shown in the item description column by pressing corresponding "Brand"

button 1202 and "Generic" button 1204, respectively. The removal quantity that is shown in text box 1206 that can be edited using the keyboard 24 in the event that more or less of an item is required at the time of removal.

The items shown in the Guided Removal Screen are organized in ascending order according to drawer/storage space location, which facilitates efficient and accurate removal from the various drawers and storage spaces in the dispensing station. Typically, items in the top drawer are highlighted first to prompt the user to remove items from that drawer. When all items in that drawer have been removed and the user closes the drawer, the control unit 18 assigns usage of the removed items to the selected patient case at block 1010 (FIG. 25) and records the transaction. Thereafter, items to be removed from the drawer below are highlighted on the Guided Removal screen 1200.

The record of the transaction, including, for example, the date, time, item description, quantity, and drawer/storage space location, is displayed on a panel 1208 of the Guided Removal screen 1200. In some instances, some items on the list may no longer be needed at the time of removal, so the user may wish to skip such items displayed in panel 1201 of the Guided Removal screen. Items to be skipped are identified by selecting the name of the items on the Guided Removal screen and selecting a "Skip Current Item(s)" button 1210. There may be situations in which the user may want to cancel removal of remaining items on the Guided Removal screen, such as when an emergency requires that other items be removed immediately. Cancellation of all items may be accomplished by selecting a "Cancel All Items" button 1212 at the bottom right of the Guided Removal screen 1200.

In a further embodiment of the present invention, the user may store the list of items to be removed so that it may be used repeatedly by the same user or other users to remove the same group of items. By selecting a predefined grouping or list, users avoid having to recreate lists for common event categories such as, for example, the delivery of a newborn child or general surgery. Such predefined item groupings or lists for certain event categories are known generally as kits.

Referring again to FIG. 25, at block 1012 the user may select a kit after selecting a patient case at block 1004. Upon pressing the "Remove by Kit" button 922 (FIG. 24), a list of kits is displayed on the touch screen 26.

A kit may be selected from a list of kits displayed on a panel 1112 labeled "Select Med by System Category" on the Medication Selection screen 1100 of FIG. 26. The kits are generally displayed by system category, such as analgesia, newborn, or general surgery. Although only one kit is provided for each of the illustrated system categories, in practice there may be multiple kits for each system category since more than one item can often be used for the same purpose and since the techniques and procedures practiced by users may differ. For instance, there may be several general surgery kits created by different users. Thus, the user that created a particular kit is identified in the panel 1112 to aid the user in selecting the appropriate kit. For example, a nurse wishing to remove items for use by Dr. John Smith in delivering a child would select the "Newborn" kit created by Dr. John Smith from panel 1112.

A kit may be also selected from a list of kits displayed on a panel 1114 labeled "Select Med by My Kit" on the Medication Selection screen 1100 of FIG. 26. This panel only includes the kits previously created and saved by the user that is currently logged onto the dispensing station 10. For example, as Dr. Green is the logged on user, all kits created by Dr. Green are displayed in panel 1114.

Returning once more to FIG. 25, after a kit is selected at block 1012 from either panel 1112 or panel 1114, the user may proceed to remove items at block 1008 under the direction of the Guided Removal screen 1200, as described above in connection with FIG. 27.

Alternatively, the user may proceed to remove items at block 1008 by first selecting individual items from the selected system kit. As shown in FIG. 28, for example, upon selecting the Analgesia system kit, the list 1102 in the center panel of the Medication Selection screen 1100 will include only items included in the Analgesia system kit. The user may then proceed to select items from the list 1102 to be included in the selected summary 1106 in the right-side panel of the Medication Selection screen 1100. When the user is ready to remove all items included in the selected summary 1106, the user may press the "Dispense" button 1116 causing the control unit 18 to indicate the location of the selected items within the dispensing station and to unlock the appropriate drawers.

From the foregoing, it will be appreciated that the system and method for storing items and tracking item usage in accordance with the principles of the invention improves the workflow of users by providing greater flexibility in storing and tracking a wide variety of items. Through a graphical user interface, users may quickly and conveniently reconfigure the number, size and location of storage spaces in dispensing station drawers. Users may also efficiently and accurately dispense items with the use of a graphical user interface or a scanner adapted to read machine-readable identifiers on drawer storage spaces and items. With resulting workflow improvements, users have more time to provide direct care to patients, which improves patient safety, and assists in reducing tracking errors.

While several particular forms of the invention have been illustrated and described, it will also be apparent that various modifications can be made without departing from the scope of the invention. For example, any variety of suitable partitions can be used to allow changes to the layout of a drawer. Also, the storage spaces can be defined by adjustable partitions or other suitable means of separating one storage space from another. As another example, any suitable filtering and sorting method may be employed to facilitate efficient use of the graphical user interface. It is also contemplated that various combinations or subcombinations of the specific features and aspects of the disclosed embodiments can be combined with or substituted for one another in order to form varying modes of the invention. For example, a virtual layout may be employed in combination with the Guided Removal screen to assist in removal of a series items in a predefined list or kit. Accordingly, it is not intended that the invention be limited, except as by the appended claims.

We claim:

1. A system for storing items and tracking item usage comprising:
 a drawer having a plurality of storage spaces adjustable to accommodate various sized items;
 an input means for inputting drawer configuration information and storage space location information;
 a control unit in operable communication with the drawer and programmed to receive inputs from a user to adjust the configuration of the drawers, including locations of the storage spaces;
 a memory in operable communication with a processor to store storage space specific information and item-specific information, the storage space-specific information including storage space location information and drawer configuration information;
 a display screen in communication with the control unit, the display screen configured to display an image representative of the storage space-specific information stored by the control unit.

2. The system of claim 1, wherein the image representative of the storage space-specific information includes a graphical representation of the drawer and locations of the storage spaces relative to one another.

3. The system of claim 1, wherein the processor is further programmed to generate a transaction record when the user inputs storage space-specific information, the transaction record comprising at least a description and a numerical quantity of items placed into a selected storage space.

4. The system of claim 3, wherein the transaction record further comprises a description and a numerical quantity of items removed from the selected storage space.

5. The system of claim 1, wherein the display screen is configured to display a preliminary image that is user-modifiable to communicate storage space-specific information to the control unit.

6. The system of claim 1, further comprising:
a machine-readable identification tag affixed to an item, and
a scanner in communication with the control unit, the scanner configured to read the tag.

7. The system of claim 6, wherein the machine-readable identification tag is configured to store and communicate item-specific information.

8. The system of claim 1, further comprising:
a machine-readable identification tag affixed to one of the plurality of storage spaces, and
a scanner in communication with the control unit, the scanner configured to read the tag.

9. The system of claim 8, wherein the machine-readable identification tag is configured to store and communicate item-specific information.

10. A system for storing items and tracking item usage comprising:
a tray having a plurality of storage spaces for storing items, one or more of the storage spaces having partitions that are user-adjustable;
a control unit configured to store storage space-specific information and item specific information, and configured to generate transaction records; and
a graphical user interface in communication with the control unit, the graphical user interface including a user-defined touch-sensitive image representative of the storage space-specific information stored by the control unit and for inputting and editing storage space-specific information.

11. The system of claim 10, wherein the touch-sensitive image depicts a graphical representation of the tray and positions of the partitions contained therein.

12. The system of claim 10, wherein when the user touches a portion of the touch-sensitive image corresponding to a selected storage space on the tray, the control unit creates a transaction record comprising at least a description and a numerical quantity of items placed into the selected storage space.

13. The system of claim 10, wherein when the user touches a portion of the touch-sensitive image corresponding to a selected storage space on the tray, the control unit creates a transaction record comprising at least a description and a numerical quantity of items removed from the selected storage space.

14. The system of claim 10, wherein the graphical user interface is configured to display a preliminary image that is capable of being modified to communicate storage space-specific information to the control unit.

15. The system of claim 10, further comprising:
a machine-readable identification tag affixed to an item, and
a scanner in communication with the control unit, the scanner configured to read the tag.

16. The system of claim 15, wherein the machine-readable identification tag is configured to store and communicate item-specific information.

17. The system of claim 10, further comprising:
a machine-readable identification tag affixed to one of the plurality of storage spaces, and
a scanner in communication with the control unit, the scanner configured to read the tag.

18. The system of claim 17, wherein the machine-readable identification tag is configured to store and communicate item-specific information.

19. A method for storing items and tracking item usage comprising:
providing a graphical representation of a current drawer configuration, the graphical representation including at least one location where a storage space may be located;
identifying a first corner of a desired storage space location;
identifying a second corner of the desired storage space location;
updating the graphical representation to show an identified storage space location including the identified first and second corners; and
storing the identified storage space location in a memory.

20. The method of claim 19, further comprising:
receiving storage space-specific information from a graphical user interface,
associating the storage space with a selected item to be stored in the storage space,
storing the selected item in the storage space,
dispensing the selected item from the storage space, and
generating a transaction record.

21. The method of claim 20, wherein receiving storage space-specific information comprises:
displaying a preliminary image on the graphical user interface, and
modifying the preliminary image on the graphical user interface into an image representative of the location of the storage space within the drawer.

22. The method of claim 20, wherein associating the storage space with the selected item to be stored in the storage space comprises scanning an identification tag on the storage space and scanning an identification tag on the selected item.

23. The method of claim 20, wherein dispensing the selected item comprises displaying on the graphical user interface a graphical image representative of the storage space-specific information and selecting a portion of the image.

24. The method of claim 20, wherein dispensing the selected item comprises scanning an identification tag on the selected item.

25. The method of claim 20, wherein dispensing the selected item comprises defining a kit of items to be dispensed and defining a sequence for removing the kit of items based on storage space locations of individual items within the kit.

26. The method of claim 25, wherein defining the kit of items to be dispensed comprises selecting individual items from the graphical user interface.

27. The method of claim 25, wherein defining the kit of items to be dispensed comprises selecting a predefined list of items from the graphical user interface.

28. The method of claim 20, wherein generating the transaction record comprises displaying on a graphical user interface a graphical image representative of the storage space-specific information and selecting a portion of the image.

29. The method of claim 20, wherein generating the transaction record comprises scanning an identification tag affixed on the selected item.

* * * * *